(12) United States Patent
Sykes et al.

(10) Patent No.: US 6,313,274 B1
(45) Date of Patent: Nov. 6, 2001

(54) PHOTOACTIVATION OF PROTEINS FOR CONJUGATION PURPOSES

(76) Inventors: Thomas R. Sykes, 4123 Ramsay Road, Edmonton, Alberta (CA), T6H 5L5; Thomas K. Woo, 7020-13 Avenue, Edmonton, Alberta (CA), T6K 3P7; Antoine A. Noujaim, 58 Wilkin Road, Edmonton, Alberta (CA), T6M 2K4; Pei Qi, 2412 104 Street, Edmonton, Alberta (CA), T6J 4R1

( * ) Notice: Subject to any disclaimer, the term of this patent is extended or adjusted under 35 U.S.C. 154(b) by 0 days.

(21) Appl. No.: 08/362,517

(22) PCT Filed: Jul. 6, 1993

(86) PCT No.: PCT/US93/06388

§ 371 Date: May 25, 1995

§ 102(e) Date: May 25, 1995

(87) PCT Pub. No.: WO94/01773

PCT Pub. Date: Jan. 20, 1994

Related U.S. Application Data

(63) Continuation-in-part of application No. 07/908,261, filed on Jul. 6, 1992, now abandoned.

(51) Int. Cl.[7] .............................. C07K 16/18; C07K 1/13
(52) U.S. Cl. ................. 530/391.3; 436/545; 436/804; 436/815; 530/391.5; 530/387.1; 530/402
(58) Field of Search ........................... 530/391.3, 391.5, 530/387.1, 402; 436/545, 804, 815

(56) References Cited

U.S. PATENT DOCUMENTS

| | | |
|---|---|---|
| 4,202,323 | 5/1980 | Zweig et al. . |
| 4,424,200 | 1/1984 | Crockford et al. . |
| 4,443,427 | 4/1984 | Reinherz et al. ............ 436/548 |
| 4,597,999 | 7/1986 | Lingwood . |
| 4,612,007 | 9/1986 | Edelson . |
| 4,625,014 | 11/1986 | Senter et al. ............ 436/547 |
| 4,689,310 | 8/1987 | Kramer et al. ............ 436/512 |
| 4,713,326 | 12/1987 | Dattagupta et al. ............ 436/501 |
| 4,716,122 | 12/1987 | Scheefers ............ 436/532 |
| 4,741,900 | 5/1988 | Alvarez et al. ............ 436/548 |
| 4,867,973 | 9/1989 | Goers et al. ............ 514/8 |
| 5,061,641 | 10/1991 | Shochat et al. ............ 436/545 |
| 5,078,985 | 1/1992 | Rhodes ............ 530/402 |

FOREIGN PATENT DOCUMENTS

| | | |
|---|---|---|
| 0271806 | 6/1988 | (EP) . |
| 0354543 | 2/1990 | (EP) . |

OTHER PUBLICATIONS

Rhodes, et al., "Technetium–99–m Labeling of Murine Monoclonal Antibody Fragments", The Journal of Nuclear Medicine, vol. 27, no. 5, May 1986, pp. 685–693.

Pandey, et al., "Photochemical linking of primary aromatic amines to carrier proteins to elicit antibody response against the amine haptens", journal of Immunological Methods, vol. 94, 1986, pp. 237–246.

Chowdhry, Vinay, "Photoaffinity Labeling of Biological Systems", Annual Review Biochemistry, vol. 48, 1979, pp. 293–325.

Galardy, et al., "Photoaffinity Labeling of Peptide Hormone binding Sites", The Journal of Biological Chemistry, vol. 249, No. 11, Jun. 1974, pp. 3510–3518.

Wickens, et al., "Free–radical mediated aggregation of human gamma–globulin", Agents and Actions, vol. 11, 1981, pp. 650–651.

Wickens, et al., "Fluorescence Changes in Human Gamma-–Globulin Induced by Free–radical Activity", Biochimica Et Biopysica Acta, vol. 742, 1983, pp. 607–616.

Lunec, et al., "Self–perpetuating Mechanisms of immunoglobulin G Aggregation in Rheumatoid Inflammation", J. Clin. Invest., vol. 76, Dec. 1985, pp. 2084–2090.

Klaus Dose, "Theoretical Aspects of the U.V. Inactivation of Proteins Containing Disulfide Bonds", Photochemistry and Photobiology, vol. 6, 1967, pp. 437–443.

Klaus Dose, "The Photolysis of Free Cystine in the Presence of Aromatic Amino Acids", Photochemistry and Photobiology, vol. 8, 1968, pp. 331–335.

*Primary Examiner*—Mary E. Ceperley
(74) *Attorney, Agent, or Firm*—Iver P. Cooper

(57) ABSTRACT

A protein containing one or more disulfide bonds, e.g., an antibody, is subjected to ultraviolet radiation to reduce one or more such bonds to reactive sulfhydryl groups; the resulting photoactivated protein is reacted with other chemical entity which is reactive with sulfhydryl, such as certain radiometals, chelating agents, drugs and toxins, so as to obtain a conjugate useful in, e.g., in vitro diagnosis, in vivo imaging, and therapy.

42 Claims, 15 Drawing Sheets

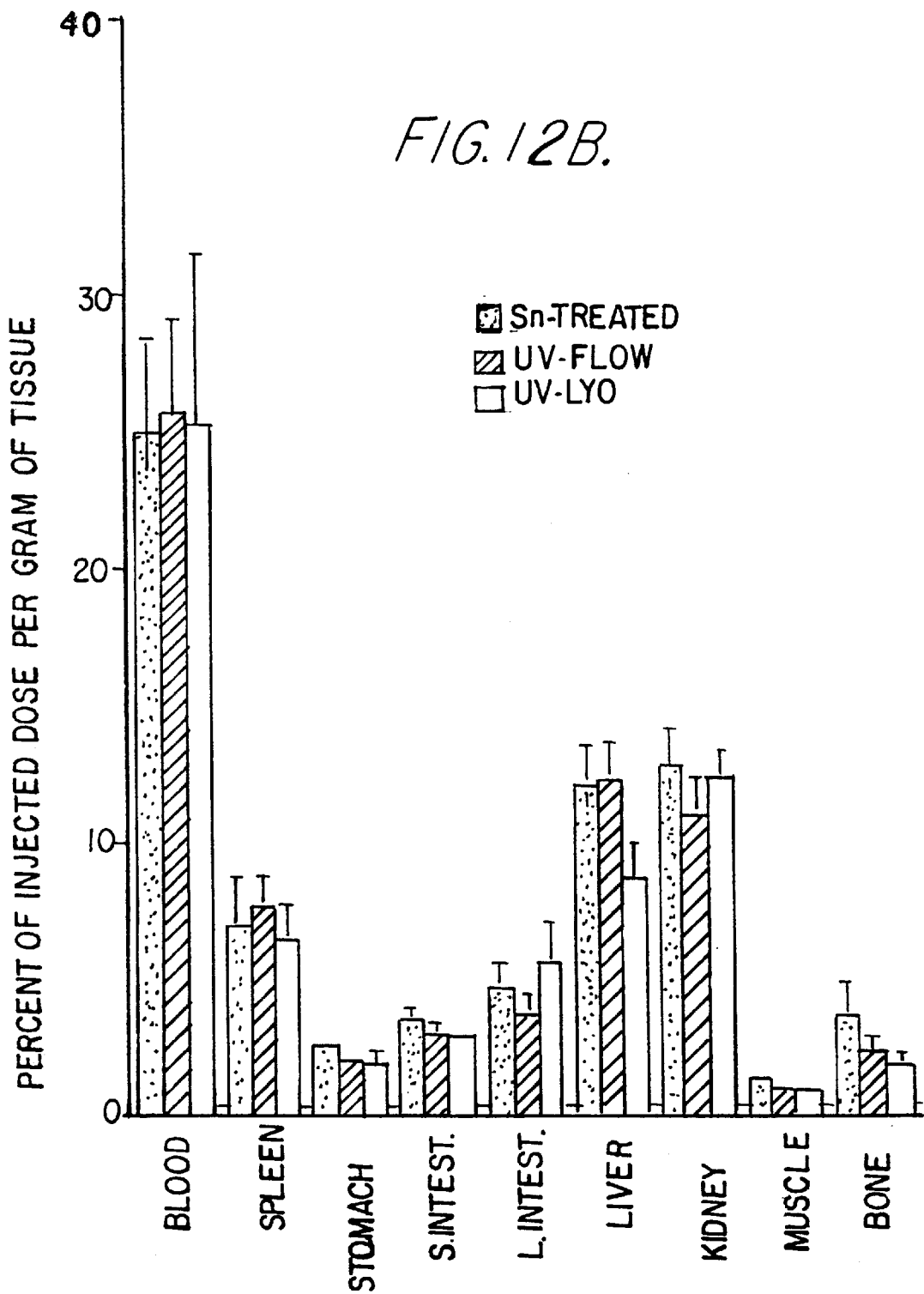

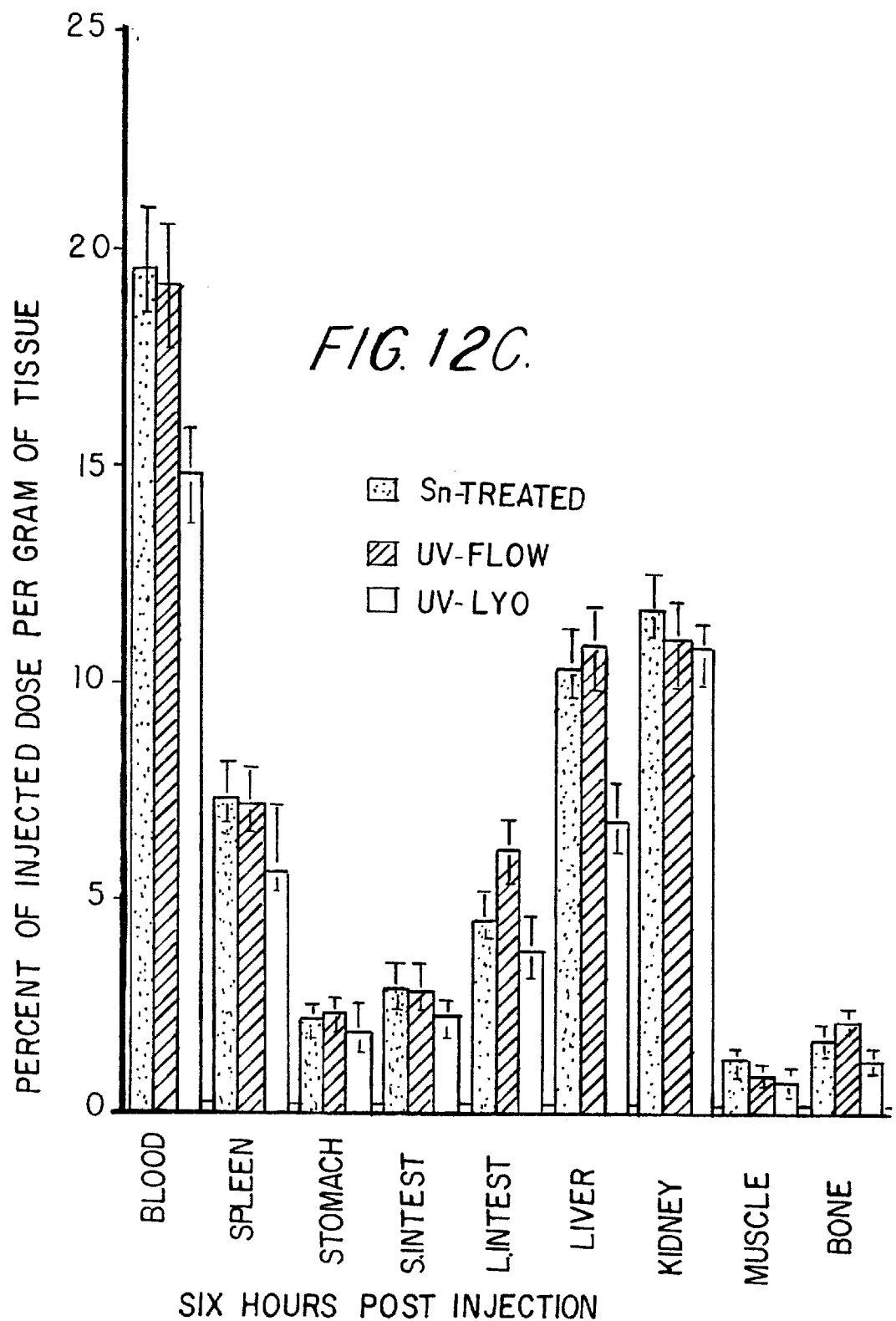

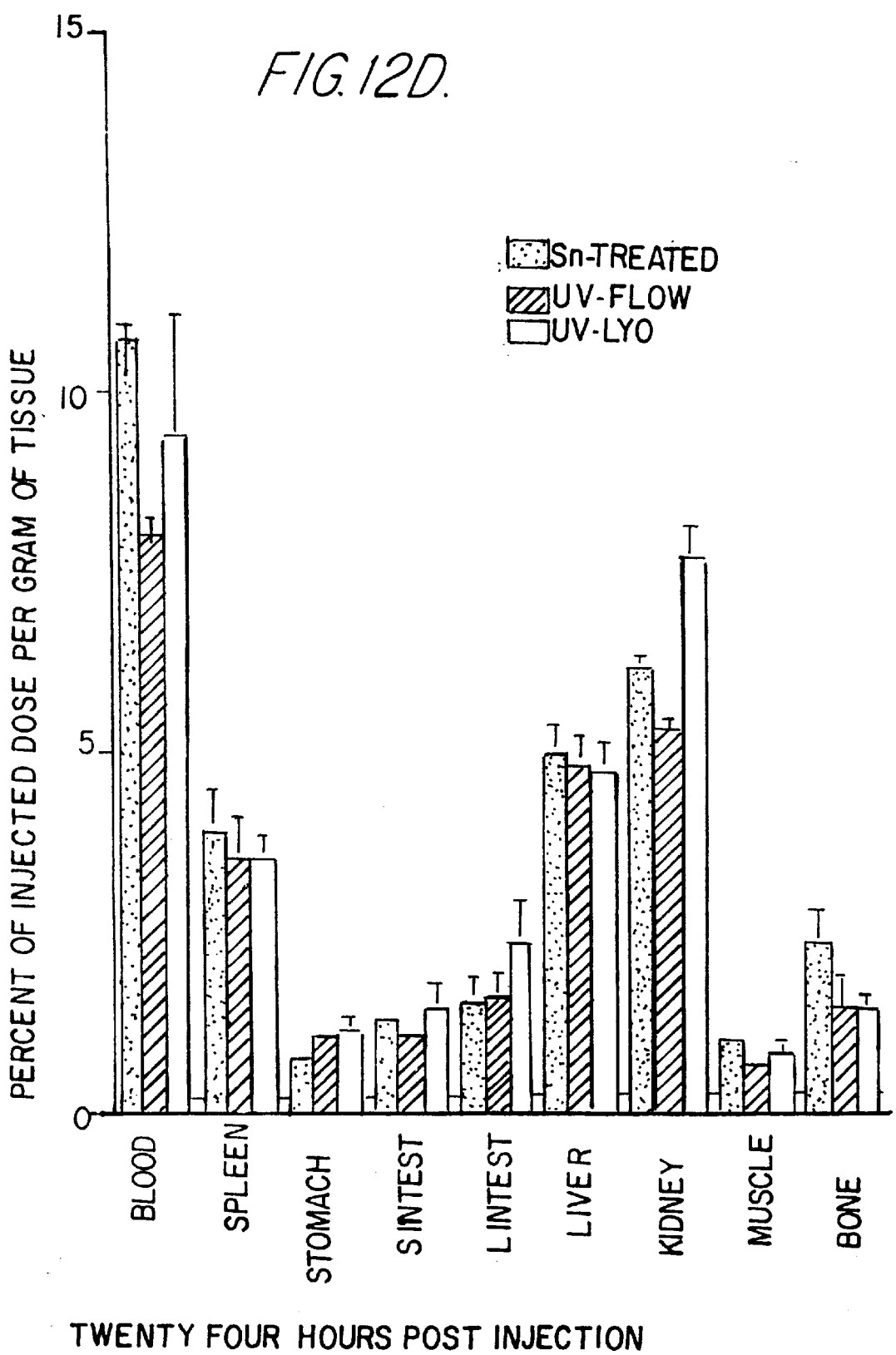

PHOTOACTIVATION OF PROTEINS FOR CONJUGATION PURPOSES

This application is a continuation-in-part of Ser. No. 07/908,261, filed Jul. 6, 1992, now abandoned.

BACKGROUND OF THE INVENTION

1. Field of the Invention

The present invention relates to the photoactivation of proteins by ultraviolet radiation, so that they may be reacted with other chemical entities, including radio-isotopes, to form useful conjugates.

2. Description of the Background Art

A. Radiolabelling of Antibodies

The conventional method of labeling antibodies with technetium (and similar radiometals) is to reduce the disulfide bonds of the antibody with a chemical reducing agent and then react the reduced antibodies with reduced pertechnetate.

Chemical reducing agents are difficult to handle due to their susceptibility to oxidation. They may cause unwanted side reactions on proteins (for example, by reducing carbonyl groups), and it may be difficult to control the extent of the reduction reaction given the need to use strong reducing reagents.

Prior to radiolabelling, the reduced antibodies must be separated from the remaining reducing reagent to stop the reaction, to remove potentially toxic substances (e.g., DTT, if used for reduction), and to avoid complexing technetium and thereby preventing it from labeling the protein. This purification process is time-consuming and may lead to loss of protein, or to re-oxidation of the protein.

Since a source of reduced technetium is required for radiolabeling, a certain amount of reducing agent must be added back to either the reduced protein or to the technetium source itself. The latter implies that the labeling process is necessarily at least two steps.

Rhodes, et al., J. Nucl. Med., 27:685 (1986 and Crockford and Rhodes, U.S. Pat. No. 4,424,200 (1984) teach a method of labelling $F(ab')_2$ fragments of antibodies with the radio-isotope Tc-99m. The fragments were incubated overnight with stannous ions (e.g., $SnCl_2$), a reducing agent, in a phthalate-tartrate buffer. This "pretinning" process converts the dimeric $F(abl)_2$ to monomeric fragments through reduction of the disulfide bonds connecting the heavy chains. The fragments are then reacted with Tc-99m.

Unfortunately, the Rhodes method has several disadvantages. First, it requires a high concentration of stannous ion to reduce the antibody. Nonetheless, Rhodes desires that about two-thirds of the stannous ions be oxidized in the reaction with the protein, the remainder serving to reduce the pertechnetate when it is added later. However, it is difficult to control the extent to which the stannous ions are involved in the reduction of the antibody. If too little stannous ion was provided, the pertechnetate will not be completely reduced by the residuum. If too much stannous ion was furnished, some will complex the Dertechnetate so that it will not bond to the antibody. Consequently, it is customary, after reducing the antibody, to purify out the residual stannous ion, and then add back a small, controlled amount to reduce the pertechnetate. The purification step of course add to the time and expense of the process. See, e.g. the discussion in Bremer, et al, EP Appl. 271,806, "Process for Producing an Organ-Specific Substance Labeled with Technetium-99m".

Rhodes, U.S. Pat. No. 5,078,985 acknowledge that his original pretinning method had "problems associated with lack of purity of the protein, continued reduction of disulfide bonds in the protein, and the formation of additional reduced protein species prior to admixture with sodium tertechnelate. Fewer stannous ions are needed to reduce pertechnetate than to reduce disulfide bonds in proteins; with some proteins, excess stannous ions cause reduction of disulfide bonds and fragmentation of the protein to less than the desired size." Consequently, Rhodes '985, taught that after the initial reduction, whether with stannous ion or a different agent such as dithiothreitol (DTT), the reduced protein should be purified to substantially remove the first reducing agent and impurities, and stannous ion added in a sufficient amount to reduce the radionuclide (the latter to be added in subsequent step).

Because the stannous ion concentration is high, the likelihood of undesired fragmentation of the antibody is increased. This is because a strong reducing agent, such as stannous ion, will reduce disulfide bonds, and the extent of such reduction, and therefore of fragmentation, is a function of concentration. The Crockford and Rhodes process is not readily adjusted to reduce unwanted fragmentation.

While the '200 patent asserts that a pH of 4.5 to 8.5 is "preferred", in our experience the upper limit on pH is actually 6. With a higher pH, stannous ion is precipitated out of solution, and therefore is unavailable for reduction. This is unfortunate, as some proteins, including certain antibodies, are more stable at a higher pH.

Rhodes' method requires long incubation times; the '200 patent calls for reaction for at least 15 hours, more preferably 21 hours. Such long reactions are inherently more vulnerable to mishaps, such as loss of temperature control or nitrogen supply, contamination, etc. Finally, its yields are lackluster; the yield reported in the Crockford '200 patent was 73% radiolabeled IgG. A more typical yield is a litte over 50% as seen in Table 2A. About 17% of Crockford's Tc was in colloidal form. Moreover, about 28% of the Tc on the antibody was "exchangeable".

Shochat, U.S. Pat. No. 5,061,641 uses the same reducing agent and buffer, but suggests that it may be helpful to contact the resulting technetium-labeled antibody with an "exogenous capping ligand", such as a mercaptoalkane or phosphane, to fill the remaining coordination sites of the radiometal and thereby stabilize it. But this patent does not address any of the other disadvantages of the Rhodes method.

B. Photoafffinity Labeling of Proteins

Photoactivatable agents, including arylazides, have been used to immobilize an antigen or antibody on a support. See Kramer, U.S. Pat. No. 4,689,310; Scheebers, U.S. Pat. No. 4,716,122; AU-A-47690/85 (organogen). Dattagupta, U.S. Pat. No. 4,713,326 photochemically coupled a nucleic acid to a substrate. Other molecules have also been insolubilized by this technique. Lingwood, U.S. Pat. No. 4,597,999. Pandey, et al., J. Immunol. Meth., 94:237–47 (1986) conjugated a haptenic primary aromatic amine (3-azido-N-ethylcarbazole) to various proteins to create a synthetic antigen.

Furthermore, one may prepare a "prodrug" or "protoxin" which is converted to the active drug or toxin by photochemical cleavage of a bridging group. Zweig, U.S. Pat. No. 4,202,323; Senter, U.S. Pat. No. 4,625,014; Edelson, U.S. Pat. No. 4,612,007; Reinherz, U.S. Pat. No. 4,443,427 (col. 4).

Photoaffinity labeling of enzymes is also known. Chowdry, Ann. Rev. Biochem., 48:293–305 (1979). In this technique, a probe compound is allowed to interact with a biomatrix in which a specific receptor or binding site is envisaged. Upon formation of the specific complex by their affinity for one another the pair are chemically linked via a reactive group on the probe. This greatly facilitates the identification and characterization of the receptor itself. The great advantage of probes incorporating a photoactive group is that the linkage process may be activated after all non-specific interactions of the probe have been eliminated and thus little or no indiscriminate binding or loss of probe through hydrolysis takes place. These photoaffinity reagents may be prepared either via synthetic routes for simple molecules or via conjugation of a photoactive ligand for more complex macromolecules.

Thus, photoaffinity labeling of peptide hormone binding sites was reported by Galardy, et al., J. Biol. Chem., 249: 350 (1974). The probes employed were aryl azides, which, when photoactivated to yield aryl nitrenes, can label any binding site containing carbon-hydrogen bonds by insertion into the C—H bond.

Biomira (Noujaim), EP Appl. 354,543 teaches the photochemical attachment of chelating groups to biomolecules, such as proteins (especially antibodies). This may be used to indirectly radiolabel a biomolecule with a chelatable ion. A chelating group is first coupled to a photoactivatable functionality. If reacted with an antibody in the presence of light, the "photochelate" will label the antibody. The disclosed activated species are carbenes, nitrenes and free radicals, though only nitrenes are exemplified.

C. Studies of Effect of Ultraviolet Radiation on Proteins

Low intensity ultraviolet irradiation of human gamma globulin has been shown to result in the generation of free sulfhydryl groups and in the aggregation of the protein. Wickens, et al., "Free radical-mediated aggregation of human gamma globulin, Agents and Actions, 11:650 (1981). Disulfide bonds are reduced at random and the resulting free sulfhydryls can re-combine with free thiol groups on other molecules to generate aggregates. Later experiments showed that other sources of oxygen free-radicals, such as a mixture of copper salts and hydrogen peroxide, had similar effects. Wickens, et al., Biochim. Biophys. Acta, 742: 607 (1983). The intrachain, rather than the interchain, disulfide bonds were deemed to be the primary targets since further fragmentation was not seen. According to Lunec, et al., J. Clin. Invest. 76: 2084 (1985), the aromatic amino acids, especially tryptophan and tyrosine, are also attacked. These researchers teach that free radical damage of IgG, through the mechanism of aggregate formation, resulted in the production of rheumatoid factors, i.e., in an autoimmune response to the aggregated antibodies. Thus, it would normally be considered undesirable to expose antibodies, for long enough periods to reduce disulfide bonds, to ultraviolet radiation.

The aforementioned findings with respect to antibodies are consistent with studies of the inactivation of disulfide enzymes (e.g., trypsin) by ultraviolet radiation; cystine disruption is likely to be a major contributing factor. Moreover, the presence of tryptophan or tyrosine residues in a given protein may contribute to the destruction of the cystine residues. K. Dose, "Theoretical Aspects of the U.V. Inactivation of Proteins containing Disulfide Bonds", *Photochem. Photobiol.* 6, 437–443 (1967); K. Dose, "The Photolysis of Free Cystine in the Presence of Aromatic Amino Acids", *Photochem. Photobiol.* 8, 331–335 (1968). As a result, ultraviolet irradiation of antibodies, which contain disulfides, is contraindicated, as it may result in loss of activity if disulfide bonds essential to antigen-binding and/or effector function are ruptured.

No admission is made that any reference or statement herein constitutes prior art, and Applicants reserve the right to challenge the accuracy of the nominal publication date of any cited publication, or of the contents thereof.

SUMMARY OF THE INVENTION

The present invention overcomes the above-noted deficiencies of the background art. More particularly, it contemplates the photochemical activation of proteins, especially disulfide-containing proteins, (e.g., antibodies), for conjugation to other chemical entities ("partners"). In one preferred embodiment, the partner is a radioisotope, such as a radiometal, especially technetium. In another preferred embodiment, the partner is another protein, a toxin, or a chelate.

The methods describe herein make possible a simple, "one pot" preparation of an activated protein. The specific examples included refer, in a non-limiting manner, to the activation and radiolabeling of proteins with technetium. The radiolabeling is rapid, with high radiolabeling yields being obtained in less than an hour. The yield, indeed, is higher than that obtained by the pretinning method with even an overnight incubation. The extent of the reaction is readily controlled, and it is not necessary to remove any of the reagents. The medium may be optimized for antibody stability, including use of buffers other than saline, and its pH may be greater than 6. In using this method to label antibodies with technetium, we typically see less than 5% colloidal Tc and less than 2% exchangeable Tc.

Surprisingly, the irradiation of the antibody does not inactivate it, or result in the formation of potentially immunogenic aggregates, though these problems would have been expected in view of the background art.

One way in which immunogenic aggregates could have been expected to form is through the reaction of the free thiols formed by the photochemical reaction to form new disulfide bonds connecting two different antibody molecules.

Another effect of the The photochemically-induced reduction of the disulfide bonds which could have been thought capable of increasing antigenicity is that it can result in an equivalent oxidation elsewhere in the antibody molecule. While the Wickens paper (Tickens, et al., Agents and Actions, 11, 650, 1981) does not identify the sites of oxidation in the antibody molecule, it nonetheless presents evidence (fluorescence data) that indicates that aromatic amino acid side chains such as those of tryptophan or tyrosine are oxidized during irradiation. In classical organic chemistry, such concomitant oxidation/reduction reactions are referred to as disproportionations. We are thus looking at an intramolecular disproportionation of the antibody. The oxidized tryptophan or tyrosine derivatives of separate antibody molecules can subsequently react to form crosslinks which may increase antigenicity or decrease antigen-binding activity.

Given the frequency of Tyr, Phe, and Trp residues in complementarity-determining regions of antibodies, one would have been led to expect that the photochemical reduction of the antibodies' disulfide bonds could have produced oxidative changes in the CDRs with the potential for considerable loss of antigen binding capacity. Moreover, certain disulfide bonds, such as those local to the variable domain, may make important contributions to antigen binding activity, and it was not possible, a priori, to state whether photochemical reduction would have cleaved these disulfide bonds.

The fact that Noujaim did not experience loss of antigen binding capacity as a result of UV irradiation of certain derivatized antibodies would nor have overcome the negative teachings of Wickens et al. Noujaim did not determine whether, as a result of the exposure to UV, his antibody had become more antigenic. Consequently, a person of ordinary skill in the art, aware of the teachings of both Wickens and Noujaim, would still have been concerned that the irradiated antibody would form immunogenic aggregates or would otherwise be altered in a manner which would activate the immune system.

In the Noujaim case, irradiation is used to effect conversion of a photosensitive molecule, such as an aromatic azido derivative, into a highly reactive intermediate, such as a nitrene. Both the reaction generating the nitrene and the subsequent attack of the carbene or nitrene are extremely rapid, so that a typical reaction time for the procedure of Noujaim is 5 min. While Noujaim teaches that the azide may be photolyzed in the presence of an antibody, Noujaim does not contemplate that the irradiation will have any effect on the antibody. Rather, the antibody is seen as a passive substrate for a chemical attack by the nitrene resulting from the photoactivation of the azide.

In contrast, in the present invention, the antibody itself is photoactlvated by UV IrradIatlon. It then reacts with partner molecules through its free thiol groups, or possibly, with reactive derivatives of its aromatic amino acids. These moieties are much less reactive than are the nitrenes (or carbenes) of the Noujaim disclosure.

It should further be pointed out that Noujaimls findings regarding retention of antigen-binding activity would not necessarily be extrapolated, by persons skilled In the art, to the preferred embodiments of the present invention. Noujaim's photolysis apparatus was a water-cooled, quartz-jacketed Hanovia UV lamp (254 nm). The reaction mixture was placed 10 cm from the center of the lamp, and the irradiation was for 1–10 minutes. In Example 2 of the present application, the source was apparently the same, but the reaction mixture was closer to the lamp (5 cm) and the exposure time was longer (30 min.). It therefore appears reasonable to surmise that the irradiation conditions of our Example 2 were more drastic than those taught by Noujaim. While Applicants do not wish to be limited to the conditions of Example 2, a person skilled in the art would be hesitant to assume that simply because the diminution of antigen binding activity observed by Noujaim was small, that this would hold true if the irradiation were longer or more intense, or with wavelengths to which antibodies are more sensitive. Wickens suggests that damage to the antibodies will increase with increasing irradiation time.

Surprisingly, despite the prolonged irradiations contemplated by the present invention, neither increases in antigenicity (whether through dimer formation or through modification of aromatic residues) nor decreases in antigen binding capacity have proven to be serious concerns. While the inventors do not wish to be bound to any theory, they believe that disulfide bonds differ in their vulnerability to photochemical reduction, and that the disulfide bonds most directly involved in antigen binding activity are also the ones least susceptible to attack. As for the aromatic residues, it appears that whatever modifications are occurring, that these do not enhance immunogenicity or interfere with antigen binding.

The appended claims are hereby incorporated by reference into this specification is a further enumeration of the preferred embodiments.

BRIEF DESCRIPTION OF THE DRAWINGS

FIGS. 12A–12D compare biodistribution of Tc-99m MAb-170, in mice, depending on the method used to prepare the radiolabeled antibody.

DETAILED DESCRIPTION OF THE PREFERRED EMBODIMENTS

The Photoactivatable Protein

Figure 1:
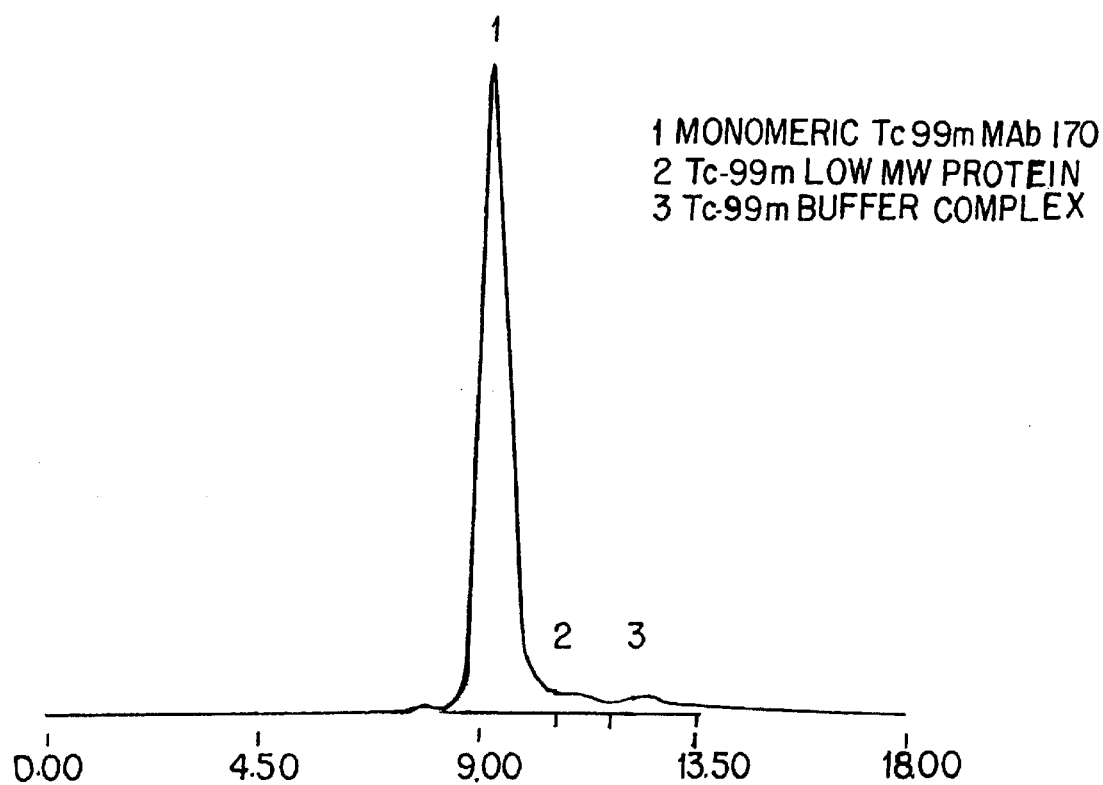
FIG. 1 shows a radiochemical chromatograph of Tc-99m labeled, irradiated MAb 170. The main peak (1) is monomeric Tc-99m MAb 170. The minor shoulders (2) and (3) are, respectively, Tc-99m Low MW protein and Tc-99m buffer complex. The ordinate is radioactivity in relative units, as measured by a flow through NaI(Tl) crystal detector, and the abscissa is time, in minutes, after injection onto the SE-HPLC column.

The protein to be photochemically activated for conjugation purposes is preferably one containing disulfide bonds non-essential for the intended use of the protein. In such a protein, a disulfide bond is present as a result of the oxidation of the thiol (—SH) side groups of two cysteine residues. These residues may lie on different polypeptide chains, or on the same polypeptide chain. As a result of the oxidation, a disulfide bond (—S—S—) is formed between the beta carbons of the original cysteine residues. After reduction, the residues should, technically speaking, be termed half-cystines, but the terms cysteine, cystine and half-cystine are often used interchangeably, the correct meaning being apparent from context. The effect of the radiation, as previously stated, is the reductive cleavage of the disulfide bonds to leave free thiol groups.

Examples of disulfide bonded proteins include antibodies, many enzymes, and certain hormones.

Antibodies.

The immunoglobulins may be used in vitro diagnosis, in vivo imaging, or therapy of diseases or conditions with distinctive antigens. The basic unit of immunoglobulin (antibody) structure is a complex of four polypeptides—two identical low molecular weight ("light") chains and two identical high molecular weight ("heavy") chains, linked together by both non-covalent associations and by disulfide bonds. Different antibodies will have anywhere from one to five of these basic units. The immunoglobulin unit may be represented schematically as a "Y". Each branch of the "Y" is formed by the amino terminal portion of a heavy chain and an associated light chain. The base of the "Y" is formed by the carboxy terminal portions of the two heavy chains. The node of the "Y" is the so-called hinge region, and is quite flexible. Five human antibody classes (IgG, IgA, IgM, IgD and IgE), and within these classes, various subclasses, are recognized on the basis of structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are far more diverse in sequence than the carboxy terminal regions, and hence are termed the variable domains. This is the part of the antibody whose structure confers the antigen-binding specificity of the antibody. A heavy variable domain and a light variable domain together form a single antigen-binding site, thus, the basic immunoglobulin unit has two antigen-binding sites. The walls of the antigen-binding site are defined by hypervariable segments of the heavy and light variable domains. Binding site diversity is generated both by sequence variation in the hypervariable region and by random combinatorial association of a heavy chain with a light chain. Collectively, the hypervariable segments are termed the paratope of the antibody; this paratope is essentially complementary to the epitope of the cognate antigen.

The carboxy terminal portion of the heavy and light chains form the constant domains. While there is much less diversity in these domains, there are, first of all, differences from one animal species to another, and secondly, within the same individual, there will be several different isotypes of antibody, each having a different function.

The IgG molecule may be divided into homology units. The light chain has two such units, the $V_L$ and $C_L$, , and the heavy chain has four, designated $V_H$, $C_H1$, $C_H2$ and $C_H3$. All are about 110 amino acids in length and have a centrally located intrachain disulfide bridge that spans about 60 amino acid residues. The sequences of the two V-region homology units are similar, as are the sequences of the four C-region homology units. These homology units in turn form domains. The two variable domains have already been mentioned; there are also four constant domains. Mild proteolytic digestion of IgG results in the production of certain fragments of interest. V-C1 is Fab; $C_H2$–$C_H3$ is Fc; (V-C1)$_2$ is (Fab')$_2$, V-C1–C2 is Fabc, and V alone is Fv.

While the variable domains are responsible for antigen binding, the constant domains are charged with the various effector functions: stimulation of B cells to undergo proliferation and differentiation, activation of the complement cell lysis system, opsonization, attraction of macrophages to ingest the invader, etc. Antibodies of different isotypes have different constant domains and therefore have different effector functions. The best studied isotypes are IgG and IgM.

The term "antibody", when used herein without further qualification, is intended to include both "intact" antibody and its various proteolytic derivatives. Antibodies may be conjugated to other molecules to produce conjugates useful in diagnosis, therapy, etc. The antibody's variable domain gives the conjugate the ability to bind specifically to particular antigenic targets.

The antibodies may be directed against antigens of medical interest, such as those associated with pathogens (incl. viruses, bacteria, fungi, and protozoa), parasites, tumor cells, or particular medical conditions. In the case of a tumor-associated antigen (TAA), the cancer may be of the lung, colon, rectum, breast, ovary, prostate gland, head, neck, bone, immune system, or any other anatomical location. Antigens of particular interest are carcinoma-embryonic antigen (CEA), human chorionic gonadotropin (hCG), alpha-fetoprotein (AFP), ferritin, Thomsen-Friedenreich antigen (TF-alpha; TF-beta), stage-specific embryonic antigen-1 (SSEA-1), human mammary tumor-associated antigen (HMTAA), oncomodulin, malignin, human placental lactogen (hPL), prostatic antigen (PA), prostatic acid phosphatase (PAP), high molecular weight-melanoma-associated antigen (HMW-MAA), thyroglobulin (Tg), tyrosine phosphokinase (TPK), epidermal growth factor (EGF), neuron-specific enolase (NSE), tissue polypeptide antigen (TPA), beta-2 microglobulin (B2M), phosphohexose isomerase (PHI), fibrin, Tn, sialyl Tn, CA-19.9; CA-125, and CA-15.3.

The term "tumor-specific antigen" as used herein will be understood to connote an antigen characteristic of a particular tumor, or strongly correlated with such a tumor. However, the current understanding in the art with respect to tumor-specific antigens is that they are not necessarily unique to tumor tissue, i.e., that antibodies to them may cross-react with antigens of normal tissue. Even where tumor-specifc antigens are not unique to tumor cells, it frequently occurs that, as a practical matter, antibodies binding to tumor-specific antigens are sufficiently specific to tumor cells to carry out the desired procedures without unwarranted risk or interference due to cross-reactions. Many factors contribute to this practical specificity. For example, the amount of antigen on the tumor cell may greatly exceed the amount of the cross-reactive antigen found on normal cells, or the antigen on the tumor cells may be more effectively presented. Therefore the term "tumor-specific antigen" relates herein to a specificity of practical utility, and is not intended to denote absolute specificity or to imply an antigen unique to the tumor.

MAb 170 (more accurately, MAb170H.82) is a murine monoclonal antibody of the IgG$_1$ kappa isotype that was produced by immunizing BALB/c mice with a synthetic glycoconjugate consisting of a Thomsen-Friedenreich (TF) beta (Galbeta1→3GalNAc) disaccharide hapten coupled to an immunologically suitable carrier (serum albumin). It was selected based on its reactivity with human adenocarcinoma tissue in vitro. It clearly reacts with adenocarcinomata of the breast, ovary, endometrium, colon, prostate and some bladder. It is described in more detail in copending Ser. No. 07/153,162, filed May 12, 1988, incorporated by reference herein, which is a continuation of Ser. No. 06/927,277, filed Oct. 27, 1986. MAb 170 has been formulated into a Tc-99m radiolabeled antibody kit (TRUSCINT AD, Biomira, Inc., Edmonton, Alberta, Canada) for radioimmunodiagnosis of adenocarcinomas. See McEwan, et al., Nuclear Medicine Communications, 13: 11–19 (1992). A hybridoma (170H82.R1808) secreting MAb 170 was deposited on Jul. 16, 1991 with the American Type Culture Collection, 12301 Parklawn Drive, Rockville, Md. 20852 USA, an International Depository Authority under the Budapest Treaty, and assigned the accession number HB 10825. This deposit should not be construed as a license to make, use or sell the hybridoma or MAb 170.

MAb B43 (more accurately, B43.13) is a murine monoclonal antibody of the IgG, kappa isotype that was produced by immunizing mice with high molecular weight mucins partially purified from ovarian ascites, and selected for its reactivity to CA 125, an ovarian carcinoma-associated antigen. It inhibits the binding of MAb OC125 to CA125. MAb B43 is reactive with CA125 antigen in biopsy tissue and in serous and endometroid carcinomas of the ovary. It has been formulated into a Tc99m-radiolabeled antibody kit (TRUSCINT OV, Biomira, Inc. Edmonton, Alberta, Canada) for radioimmunodiagnosis of ovarian carcinomas. See Capstick, et al., Int. J. Biol. Markers, 6: 129–135 (1991).

Reference to these two antibodies should not be construed as a limitation on the generality of the present invention.

The antibody may be a polyclonal antibody or a monoclonal antibody. When the subject is a human subject, the antibody may be obtained by immunizing any animal capable of mounting a usable immune response to the antigen. The animal may be a mouse, rat, goat, sheep, rabbit or other suitable experimental animal. The antigen may be presented in the form of a naturally occurring immunogen, or a synthetic immunogenic conjugate of a hapten and an immunogenic carrier. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced.

Disulfide-Bonded Enzymes.

Disulfide bonded enzymes include trypsin, chymotrypsin, aldolase, papain, and glyceraldehyde phosphate dehydrogenase. These enz-ymrs may be conjugated to other molecules for use, e.g., as labels.

Other Disulfide-Bonded Proteins.

These include albumin, transferrin, and somatostatin. Albumin can be conjugated to radioisotopes and used as a blood pool agent. Transferrin could be labeled with radio- isotopes and used to image transferrin receptors; some tumours are known to have large amounts of transferrin receptors. Somatostatin could be labeled with radioisotopes and used for tumor imaging.

The sulfhydryl/disulfide composition of several proteins is given in Table 109A.

Non-Disulfide Bonded Proteins.

The present invention may also be used to photoactivate non-disulfide bonded proteins, such as pre-albumin and protein A, that contain residues (e.g., aromatic residues) which are made more reactive by reaction with free radicals generated by photolysis.

Irradiation

The protein to be photoactivated is irradiated with ultraviolet radiation. Ultraviolet radiation is generally defined as that portion of the electromagnetic spectrum running from 10 to 400 nm wavelength. However, the quanta of shorter wavelengths are more energetic and therefore more potentially damaging to the protein. Preferably, the protein is irradiated with ultraviolet radiation which is primarily, e.g., at least 90%, more preferably at least 99%, of wavelengths in the range of 250–320 nm. Desirably, the radiation includes the wavelengths 270–320 nm, and, more desirably, is primarily of those wavelengths.

Ultraviolet radiation may be generated by any convenient source, such as a hydrogen or deuterium discharge lamp, a xenon arc lamp or a mercury vapour lamp. The lamp may be provided with a fluorescent coating so as to alter the effective wavelength of the light emitted by the lamp. For example, the internal output may be 254 nm, but may cause a coating to fluoresce at a longer wavelength, which is what is externally emitted.

To filter out undesired wavelengths, a suitable filter may be employed. Quartz transmits UV light of 190–400 nm, while borosilicate glass has a UV transmission spectrum of 300–400. Other materials which selectively transmit ultraviolet radiation include window glass, optical (white crown) glass, Vycor, quartz crystal, clear fused quarts, suprasil, synthetic sapphire, natural fluorite, synthetic lithium fluoride and plexiglass (polymethylmethacrylate). Both broad and narrow band filters are known in the art.

The filter may be incorporated into the lamp unit, or placed in the light path between the vessel and the source. Alternatively, the protein may be placed in a vessel formed wholly or partially of the filter material. It is possible that the disulfide bonds are especially sensitive to highly specific wavelengths, in which case a narrow band pass filter may be useful to minimize radiation damage to the protein. For further information on ultraviolet filters, see Calvert and Pitts, Jr., *Photochemistry*, pp. 686–798, Chapter 7, "Experimental Methods in Photochemistry" (John Wiley & Sons, N.Y.: 1966).

The effective intensity of the radiation at the target site is a function of the source intensity, the distance from the source to the reaction vessel, and the degree of absorbance of the radiation by the lamp filter and vessel walls. It is generally most convenient to adjust the effective intensity by moving the subject closer to or farther from the source, rather than by changing the source or the thickness of the filters in the light path. However, any of these parameters may be modified as desired. The overall degree of photoactivation is a function of the intensity of the radiation and the irradiation time, as well as the susceptibility of the protein to photoactivation with the wavelengths employed. Like the effective intensity, the irradiation time is readily modified. For any given protein, it is contemplated that the intensity and irradiation time will be systematically varied to identify the optimum value.

If a protein is particularly sensitive to irradiation with particular UV wavelengths, the reaction can be slowed down by filtering out, at least to some degree, those wavelengths. Contrariwise, if a protein is refractory, the intensity and duration of the irradiation at the wavelengths to which the protein is most sensitive may be increased.

Preferably, the source is placed 1–10 cm, more preferably about 5 cm, from the reaction vessel. This vessel is desirably formed of quartz or of borosilicate glass. The irradiation time is typically 5–100 minutes, preferably over 10 minutes and under 60 minutes, more preferably over 15 minutes, still more preferably at least about 20 minutes. The protein concentration is usually 1–10 mg/ml, more preferably about 6 mg/ml. The pH is typically 4–9, more preferably 6–7. When pertechnetate is the partner, it is preferably reduced with 5–100 $\mu$g Sn, more preferably about 10–30 $\mu$g.

The reaction medium may also affect the progress of the photoactivation. In particular, the pH of the medium, and the presence or absence of sensitive amino acids such as tryptophan and tyrosine, of free radical inhibitors such as glutathione, dithiothreitol and the like, or free radical generators like peroxides, may have a positive or negative effect. It is known that the disulfide bond is more susceptible to reduction at pH 8. Around this pH the effect of UV radiation should be more effective than at lower pHs. If the UV energy is absorbed by adjacent amino acids such as tyrosine or tryptophan and transferred down to the disulfide bond of cystine, then the absence of these amino acids would reduce the number of SH groups generated. If the UV energy is producing free radicals (as it is thought), then free radical inhibitors will decrease the number of SH groups formed; likewise free radical activators or generators should generate more SH groups. The addition of ascorbic acid (a free radical scavenger) to the protein solution prior to UV irradiation drastically reduces the Tc-99m radiolabeling yields, implying a free radical mechanism may be involved.

Photoactivation of production quantities of material can be accomplished by irradiating a vessel holding a homogeneous solution of the MAb or other target, with continuous stirring during irradiation, using commercially acquired UV sources. Alternatively, the bulk solution can be circulated through an appropriate glass tube passing around or through the UV source (must be custom made). The material can also be vialled and then irradiated via on-line (i.e., assembly line through one UV source) or bulk (irradiate all vials at once) irradiation.

Once the protein has been photoactivated by irradiation, it may be conjugated immediately, or it may be stored for future use. The conjugation reactions may be carried out in any buffer appropriate for maintaining the desired pH range. The stability of the material may be increased, if desired, by lyophilization, or by addition of thiol stabilizers.

The Conjugation "Partner"

The photoactivated protein may be conjugated with any "partner" of interest, including a radiometal salt, drug, toxin, chelate, etc.

When photoactivation of the protein results in formation of free thiol groups, the protein may be conjugated with any sulfhydryl reactive agent. Preferably, the agent is one which is substantially specific for free thiol groups. It is certainly not necessary that the agent be an extremely reactive species such as a nitrene or carbene.

Sulfhydryl-Reactive Radiometals.

Radiometals which can be bound to proteins using the present method are those which bind tightly to sulfhydryl groups. Generally, these will be metal ions which form relatively insoluble sulfides in the conventional qualitative analysis schemata. These include, but are not limited to, ions of Tc-99m, Re-186, Re-188, Cu-64, Cu-67, Hg-195, Hg-197, Hg-203, Pb-203, Pb/Bi-212, Zn-72, $\mu$g-105, $\mu$g-111, Au-198, Au-199, Cd-115, Cd-115m, Sn-117, Sn-125, and the like. Radiometals having a gamma emission energy in the range of about 50–500 KeV are useful for scintigraphy. Positron emitters can also be used for imaging applications. Beta and alpha emitters are useful for therapy. Preferably, the radiolabeling yield is greater than 80%, and, more preferably, is greater than 90%. Desirably, these preferred yields are achievable with proteins which were irradiated for not more than about two hours, and more preferably not more than about one hour.

In one embodiment, the partner is a pertechnate, rhennate, or other radioisotopic agent of similar chemistry. In general, the pertechnetate or rhennate will be reduced so that it will react with the free thiol groups of the protein. Suitable reducing agents include sources of stannous ion, such as stannous chloride and stannous tartrate; stannous tartrate is preferred because the tartrate anion stabilizes the Sn-Tc complex. Other reducing agents known in the art include 2-mercaptoethanol,1,4-dithiothreitol,2,3-dihydroxybutane-1.4-dithiol,2-aminoethanethiol HCl, 2-mercaptoethylamine, thioglycolate, cyanide and cysteine. The amount of the reducing agent, and the incubation time, are adjusted in the light of the reducing agent employed. The stannous ion may be added to the protein prior to photoactivation, and the pertechnetate added afterward, or the protein may first be photoactivated, and the stannous ion and pertechnetate added after irradiation. Typically only small quantities of reducing agent are required, as it is used only to reduce the radiometal and not the antibody or other partner, so that purification to remove excess tin is unnecessary.

Technetium-99m is a preferred radiolabel for scintigraphy because of its ready availability and ease of preparation from commercial pertechnetate generators.

Technetium labeling of the sulfhydryl-containing protein is generally effected by conventional methods. Pertechnetate is obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinary skilled artisan.

Pertechnetate is generally used at an activity of about 0.2–10 mCi/ml in saline, e.g., 0.9% ("physiological") saline, buffered at a pH of about 3–7, preferably 3.5–5.5, more preferably about 4.5–5.0. Suitable buffers include, e.g., acetate, tartrate, phthalate, citrate, phosphate and the like.

Rhenium is found just below technetium in the periodic table and has the same outer shell electronic configuration. Rhenium and its compounds are expected to have very similar chemical properties to technetium and its analogous compounds. In fact, rhenium compounds behave similarly to technetium compounds insofar as reduction and chelation are concerned but their greater susceptibility to oxidation requires greater care in handling.

The radioisotope Re-186 is attractive for both imaging and therapy. It has a half-life of about 3.7 days, a high LET beta emission (1.07 MeV) and a convenient gamma emission energy (0.137 MeV). Rhenium may be produced from perrhenate, and the reduced rhenium ions can bind non-specifically to protein. Accordingly, a method for Re-186 labeling of proteins, wherein the reduced perrhenate is bound to sulfhydryl groups of a protein molecule such as an antibody, would be advantageous. Re-188 is a generator-produced beta and gamma emitter with a half-life of about 17 hours and could be useful for imaging and therapy.

Rhenium labeling will be effected in substantially the same manner as technetium labeling, with special care being taken to ensure the absence of air or other source of oxygen from the system. Re-186 is produced in the form of sodium perrhenate by use of a generator analogous to currently available technetium generators.

By "reduced pertechnetate" or "reduced perrhenate" is meant the species of technetium or rhenium ion formed by chemical reduction of pertechnetate or perrhenate and chelated by the thiol group(s). It is generally thought that reduced pertechnetate is in the form of Tc(III) and/or Tc(IV) and/or Tc (V) in such chelates and that reduced perrhenate is in the form of Re(III) and/or Re (IV) and/or Re(V), but higher or lower oxidation states and/or multiple oxidation states cannot be excluded and are within the scope of the invention. Copper will normally be in the form of Cu(II), although Cu(I) and/or Cu(II) are not excluded. Mercury will normally be in the form of Hg(I) and/or Hg(II). Lead/bismuth will normally be in the form of Pb(II) or Pb(IV).

Reduction is effected by any of a variety of conventional reducing agents, preferably stannous ion generally in aqueous solution. Other suitable reducing agents include, e.g., dithionite, borohydride, ferrous ion, formadine sulfonic acid, and the like. It will be appreciated that stannous ion can be generated in situ from tin metal, e.g., foil, granules, powder, turnings and the like, by contact with aqueous acid, e.g., HCl.

Copper ions are also tightly chelated by sulfur chelators. Cu-67 is another attractive radionuclide for imaging and therapy. It has a half-life of about 2.6 days, and is a beta (0.570 MeV) and gamma emitter (0.185 MeV), although the beta energy is relatively low. Cu-67 is relatively expensive and not readily available at present, although such conditions can change as demand evelops. It has the advantage that it forms tight chelates with thiols. The labeling is simple and rapid, and requires no reducing agent for the radiometal.

Copper labeling will be effected by reaction of a thiol-containing protein with a solution of copper ions, normally Cu(II) ions, in the form of a convenient salt, e.g., chloride, citrate, tartrate or the like, either as available or by mixing of e.g., the chloride with, e.g., sodium, potassium or ammonium citrate, tartrate or the like. Cu-67 is currently available as $CuCl_2$ from Oak Ridge National Laboratories, Tennessee, or from Los Alamos National Laboratories, N. Mex. Zinc, silver, gold and cadmium isotopes would chelate SH groups in a manner similar to copper.

Other radionuclides with similar chelation behavior to copper, e.g., mercury and lead, also could be bound to thiol-containing compounds according to the method of the invention. Hg-197 has a half-life of about 1.5 days, and emits gamma radiation in an energy range of 78–268 KeV, and Pb-203 is a strong gamma-emitter at about 275 KeV, with a half-life of about 51 hr, making them suitable for gamma scintigraphy. Bi-212 is an alpha emitter with a half-life of about 1 hr and an energy of 6.09 MeV, making it of considerable interest for in vivo therapy. It is produced in situ from a Pb-212 precursor with emission of gamma radiation of 239 KeV, with a half-life of about 10.6 hr. Thus, antibody conjugates for Bi-212 therapy will be Pb-212 labeled conjugates, and the short-hand notation lead/bismuth or Pb/Bi is used herein to indicate this. Chelation to the antibody protein is effected analogously to Cu-67 labeling.

Mercury radioisotopes are normally available as $HgCl_2$ or as $Hg(NO_3)_2$, e.g., from Oak Ridge National Laboratories.

Lead/bismuth radioisotopes are normally available from Argonne National Laboratories in the form of supported radon generator.

It will be understood that the invention is not limited to the exemplified radiometal ions, but is generally applicable to ions that bind tightly to sulfhydryl groups.

Stable isotopes may also be conjugated to proteins for therapeutic (e.g., Au for arthritis) or diagnostic (e.g., colloidal Au compounds for electron microscopy) purposes.

Chelates.

Chelates may be used to associate an antibody with chelatable substances, such as certain radioisotopes, which cannot be directly reacted with the photoactivated antibody. The present invention is not limited to any particular chelating agent. While, EDTA and DTPA derivatives are preferred, many chelating agents are known. See Mears, U.S. Pat. No. 4,678,667; Wieder, U.S. Pat. No. 4,352,751; Hnatowich, U.S. Pat. No. 4,479,930; Meares, U.S. Pat. No. 4,043,998; Ueda, U.S. Pat. No. 4,564,742; Davidson, U.S. Pat. No. 4,673,562; Hnatowich, U.S. Pat. No. 4,668,503; Arano, U.S. Pat. No. 4,559,221 and Costa, U.S. Pat. No. 3,809,632. Besides EDTA and analogous polycarboxylic acids, the macrocyclic chelators are of particular interest. The chelating agent is derivatized, if necessary, so as to react with the free thiols of the photoactivated protein while retaining its chelating function. The following table shows ions chelated by various agents.

| Examples of Derivitazible Chelatating Agents | Example of Chelatable Ions |
| --- | --- |
| EDTA | $^{111}$In, $^{67}$Ga, $^{99m}$Tc, $^{90}$Y |
| DTPA | $^{99m}$TC, $^{111}$In, $^{67}$Ga, $^{90}$, $^{153}$Sm |
| MA-DTPA | $^{111}$In, $^{67}$Ga, $^{99M}$TC, $^{90}$Y, $^{153}$Sm |
| CA-DTPA | $^{111}$In, $^{67}$Ga, $^{99M}$TC, $^{90}$Y, $^{153}$Sm |
| TETA; DOTA | $^{111}$In, $^{67}$Ga, $^{90}$Y |
| DADS | $^{99m}$TC, $^{136}$Re, $^{188}$Re $^{153}$Sm |

EDTA = ethylenediaminetetraacetic acid
DTPA = diethylenetriaminepentaacetic acid
MA-DTPA and CA-DTPA = Methylene Adduct and Cyclic Anhydride.
TETA and DOTA = not acronyms for chemical name; just the abbreviation given for these two chelates
DADS = diaminodisulfur Drugs.

Suitable drugs include antibiotics such as adriamycin, antitumor agents such as methotrexate, 5-fluorouracil and cis-platinum, and antiparasitic agents such as pentamidine isethionate. When an antibody is conjugated to such a drug, it serves to direct the drug to the sites where the corresponding antigen occurs.

Toxins.

Toxins are usefully conjugated to antibodies specific for antigens associated with tumor, parasite or microbial cells. The toxin may be e.g., a plant (e.g., ricin or abrin), animal (e.g., a snake venom), or microbial (e.g., diphtheria or tetanus toxin).

Besides antibodies, the drugs or toxins may be conjugated to other carrier proteins, such as albumin.

Sulfhydryl Reactive Agents

A molecule which is not inherently sulfhydryl reactive may still be conjugated to the photactivated proteins of the present invention by means of a bifunctional crosslinking agent which bears both a group reactive with the molecule of interest and a sulfhydryl reactive group. This agent, may be reacted simultaneously with both the molecule of interest (e.g., through an amino, carboxy or hydroxy group) and the photoactivated protein, or it may be used to derivatize the molecule of interest to form a partner molecule which is then sulfhydryl reactive by virtue of a moiety derived from the agent, or it may be used to derivatize the photoactivated protein to make it reactive with the molecule of interest.

Sulfyhdryl reactive agents include alpha-haloacetyl compounds such as iodoacetamide, maleimides such as N-ethylmaleimide, mercury derivatives such as 3,6-bis-(mercurimethyl)dioxane with counter ions of acetate, chloride or nitrate, and disulfide derivatives such as disulfide dioxide derivatives, polymethylene bismethane thiosulfonate reagents and crabescein (a fluorescent derivative of fluorescein containing two free sulfhydryl groups which have been shown to add across disulfide bonds of reduced antibody).

Alpha-haloacetyl compounds such as iodoacetate readily react with sulfhydryl groups to form amides. These compounds have been used to carboxymethylate free thiols. They are not strictly SH specific and will react with amines. The reaction involves nucleophilic attack of the thiolate ion resulting in a displacement of the halide. The reactive haloacetyl moiety, X—$CH_2$CO—, has been incorporated into compounds for various purposes. For example, bromotrifluoroacetone has been used for F-19 incorporation, and N-chloroacetyliodotyramine has been employed for the introduction of radioactive iodine into proteins.

Maleimides such as N-ethylmaleimide are considered to be fairly specific to sulfhydryl groups, especially at pH values below 7, where other groups are protonated. Thiols undergo Michael reactions with maleimides to yield exclusively the adduct to the double bond. The resulting thioether bond is very stable and cannot be cleaved under physiological conditions. They also react at a much slower rate with amino and imidazoyl groups. At pH 7, for example, the reaction with simple thiols is about 1,000 fold faster than with the corresponding amines. The characteristic absorbance change in the 300 nm region associated with the reaction provides a convenient method for monitoring the reaction. These compounds are stable at low pH but are susceptible to hydrolysis at high pH.

See generally Wong, Chemistry of Protein Conjugation and Cross-linking; CRC Press, Inc., Boca Raton, 1991: Chapters 2 and 4).

Conjugates and Their Uses

In vitro Immunodiagnosis.

In one embodiment, an antibody is conjugated to a detectable label for use in in vitro immunodiagnosis. The label may be a radiolabel, fluorophore, or enzyme which is directly or indirectly conjugatable to a free thiol group of the photoactivated antibody. The sample may be of clinical (e.g., blood, urine, semen, or cerebrospinne fluid, or a solid tissue or organ or nonclinical soil, water, food) nature. The assay may be qualitative or quantitative, and in any desired format, including sandwich and competitive formats. Numerous immunoassay formats, labels, immobilization techniques, etc., are disclosed in the following publications, hereby incorporated by reference herein: O'Sullivan, Annals Clin. Biochem., 16:221–240 (1976); McLaren, Med. Lab. Sci., 38:245–51 (1981); Ollerich, J. Clin. Chem. Clin. Biochem., 22:895–904 (1984); Ngo and Lenhoff, Mol. Cell. Biochem., 44:3–12 (1982).

Immunoimaging.

An immunoconjugate may also be used for in vivo immunoimaging. For this purpose, the antibody must be labeled by means which permit external visualization of its position. Typically, an immunoimaging agent will be an antibody labeled directly (as with Technetium) or indirectly (as with chelated Indium) with a suitable radioisotope. After injection into the patient, the location of the conjugate may be tracked by a detector sensitive to particles emitted by the radiolabel, e.g., a gamma-scintillation camera in the case of a gamma emitter.

Immunotherapy.

For immunotherapy, the antibody may be conjugated to a suitable radioisotope, drug or toxin.

In Vivo Use, Generally, Whether for immunoimaging or for immunotherapy, the conjugate must be introduced into the patient. Preferably, it is introduced by injection. Typically, the agent is administered intravascularly (intravenously or intraarterially) or intrathetically, often by infusion. In additon, in appropriate cases the conjugate may be introduced subcutaneously, submucosally, intramuscularly, intracranially, or by other accepted routes of drug administration.

Further discussion of techniques of immunoimaging and immunotherapy is found in standard works such as Chatal, *Monoclonal Antibodies in Immunoscintography* (CRC Press: 1989); Magerstadt, *Antibody Conjugates and Malignant Disease* (CRC Press 1981); and Burchiel et al., *Radioimmunoimaging and Radioimmunotherapy* (Elsevier). A more general review of immunological methods appears in Harlow and Lane, *Antibodies: A Laboratory Manual* (Cold Spring Harbor Laboratory: 1988).

Miscellaneous.

Other proteins may be used in a similar manner to an antibody as a targeting agent for diagnosis, imaging or therapy, when they have sufficiently specificity and affinity for an appropriate marker. See, e.g., Bakker, et al., Receptor scintigraphy with a Radioiodinated somatostatin analog: Radiolabeling, Purification, Biologic Activity and in Vivo Application in Animals. J. Nucl., Med., 31: 1501–1509, 1990. Enzymes, lectins, and various biological receptors can serve as binding agents. TPk, EGF, NSE, TPA, B2M, PHI and fibrin are known to be taken up preferentially by certain tumors.

Other Activation Methods

Lunec, et al. report the formation of IgG aggregates by three methods: (a) a mixture of copper sulfate and hydrogen peroxide, (b) arachidonic acid and (c) photolysis. The mechanism is thought to be through the generation of free radicals that attack disulfides and cause disruption of the molecular structure of the molecule. They also suggest the use of enzymatic processes (e.g., superoxide dismutase, catalase and glutathione peroxidase) to generate free radicals. The present invention extends to the enhancement of photoactivation of disulfide-containing proteins by methods, other than photolysis, which generate free radicals which attack disulfides.

EXAMPLES

Materials and Methods for Examples 1–11

A. UV Apparatus

A Conrad-Hanovia low pressure quartz mercury-vapor lamp (Ace Cat #12128) with a water cooled quartz jacket was used. Samples were irradiated for various lengths of time at a distance of 3 cm from the water jacket (5 cm from the source).

B. Radiochemical Analysis

The radiolabelled proteins were analyzed by size exclusion high pressure liquid chromatography (SE-HPLC) using a 7.8×300 mm TSK-3000SW analytical column and modified sofLt gel chromatography using a Sephadex (TM) G-50 spin-column. The SE-HPLC column is useful for quantitating relative amounts of aggregates, monomeric protein; fractionation products, unreacted reduced technetium complex, free pertechnetate and bound reduced technetium species. The Sephadex (TM) G-50 spin column is a simple and fast method for determining the percent stable protein bound radioactivity.

C. Radioimmunoassay (RIA)

To evaluate the immunoreactivity of Mab 170 after photolysis and subsequent radlolabelling, an RIA utilising a rabbit anti-Meb 170 antibody was immobilised on polystyrene tubes. Immunoreactivity indices were obtained by analysing the competition of the various dilutions of the test or reference sample with I-125 MAb 170. The index was derived from the ratio of the concentration of reference standard that gave 50% inhibition to the concentration of the test sample that gave 50% inhibition:

$$\text{Immunoreactivity Index} = \frac{\text{IC-50 Standard}}{\text{IC-50 Sample}}$$

Example 1

Radiolabelling of Bovine Serum Albumin (BSA) and Human Transferrin

The first radiolabelling experiment using UV irradiation was carried out on BSA and human transferrin. Three different concentrations of BSA or human transferrin solution (1, 5, 10 mg/ml) in 0.05 M phosphate buffer pH 7.0 were prepared. Two hundred Al of the protein solution was pipetted into a 12×75 mm quartz test-tube and irradiated as described in method (A) above for 0, 5, 15 or 30 minutes. After the irradiation, 100l of stannous tartrate solution (>20 µg of $Sn^{+2}$) was added, followed by 300 µl of Tc-99m sodium pertechnetate. The mixture was allowed to incubate for 30 minutes and was then analysed by Sephadex G-50 spin column to determine the % stable protein radiolabelling. The results are summarised in table 1.

The results show that there is an increase in the percent radiolabelling of the proteins with reduced pertechnetate after UV irradiation. At higher protein concentrations, the reaction is more efficient, resulting in higher percent radiolabelling with a shorter irradiation time.

Example 2

UV Irradiation of MAb 170 in Quartz Test Tubes

MAb 170 (Biomira, Inc., Edmonton) at 6 mg/ml in 0.05M PBS pH 7.0 was irradiated under the same setup as in method (A) above. The MAb (200 µl) was irradiated in a quartz test tube (12×75 mm) for 30 minutes and then 100 µl of stannous tartrate was added followed by 300 µl of Tc-99m sodium pertechnetate. The reaction mixture was assayed by SE-HPLC 30 minutes later. The percentage of radiolabelling species included 18% MAb aggregates, 49.3% monomeric MAb, 9.0% low molecular weight protein species and 23.0% Tc-99m buffer complex and Tc-99m pertechnetate.

Example 3

UV irradiation of MAb 170 in Borosilicate Class Vial

A nitrogen-purged 2 ml borosilicate glass tubular vial containing 200 µl of MAb 170 (6 mg/ml) and 10 µl of 0.1 M tartrate with 5 mM stannous chloride was irradiated for 30 minutes under the same setup as in method (A) above. An equal volume of Tc-99m sodium pertechnetate was then added to the vial. After 30 minutes, the reaction mixture was analysed by Sephadex (TM) G-50 spin column. The SE-HPLC chromatogram obtained is shown in FIG. 1.

The results indicate that over 950 of the Tc-99m radioactivity is bound to the protein in the MAb 170 reaction. The process is mild and does not result in excessive radiolabeled fragments or aggregates in the preparation, as shown by FIG. 1.

Example 4

UV Absorption Spectrum of Quartz Test Tube and Borosilicate Class Vial

The UV absorption spectra of quartz and borosilicate glass test tubes were measured by an HP8452 UV/Vis spectrophotometer. The quartz glass showed good transmittance of UV in the 190 to 400 nm range. The borosilicate glass test tube had high absorbance below 300 nm so the bulk of the irradiation is being carried out with wavelengths greater than 300 m UV. The difference in UV adsorption seen with the two types of glass indicate that the overall effects on the protein may be variable since shorter wavelengths may produce more damage than longer wavelengths. The preferred vessel for irradiation is a borosilicate glass test tube or tubular vial.

Example 5

Optimisation of Amount of Stannous Ion for Tc-99m Radiolabelling of MAb 170 Using UV Irradiation MAb 170 (6 mg/ml) was mixed with different amounts of stannous tartrate (containing 5 to 4 µg of $Sn^{+2}$) in a 2 ml nitrogen purged borosilicate glass tubular vial. The vial was then irradiated under the same setup as in method (A) above for 60 minutes. An equal volume of Tc-99m sodium pertechnetate was added and the percent radiolabelling was measured by Sephadex G-50 spin-column after 30 minutes. The results are summarised in table 2.

It is obvious from the data that the percent radiolabelling decreases with increasing amount of $Sn^{+2}$. The optimum amount of $Sn^{+2}$ is in the range of 5 to 20 pg. The decrease in radiolabelling yield is probably due to the competition between the irradiated protein and the Tc-99m-Sn complex formed at high Sn concentrations.

Example 6

Effect of Duration of UV Irradiation on Tc-99m Radiolabelling of MAb 170 and MAb B43

Mab 170 was pretinned by the Rhodes method and then reacted with pertechnetate. Pretinning buffer solution comprised 0.005 M $Sn^{+2}$ in 40 mM KH phthalate, 10 mM NaK tartrate, pH 5.6. The antibody had a starting concentration of 1.7 mg/ml. Three parts antibody solution were mixed with two parts pretinning buffer solution to give a final protein concentration of I mg/ml antibody and a final $Sn^{+2}$ concentration of 237 mg/ml. The reaction vial was purged with nitrogen, sealed and incubated at room temperature up to 24 hours. Sampling was done at 1, 3, 6, 12 and 24 hours. At the end of the 24 hour incubation, the remaining pretinned antibody solution was aliquoted in 2 mg aliquots and stored at −20° C. until used. Tc-99m labeling was accomplished by adding 2 mCi of Tc-99m in 0.5 ml of saline. After 30 minutes reaction time, the vial was analysed using SE-HPLC and Sephadex G-50 spin column. This conventional labeling method was compared with photoactivation.

Figure 2:
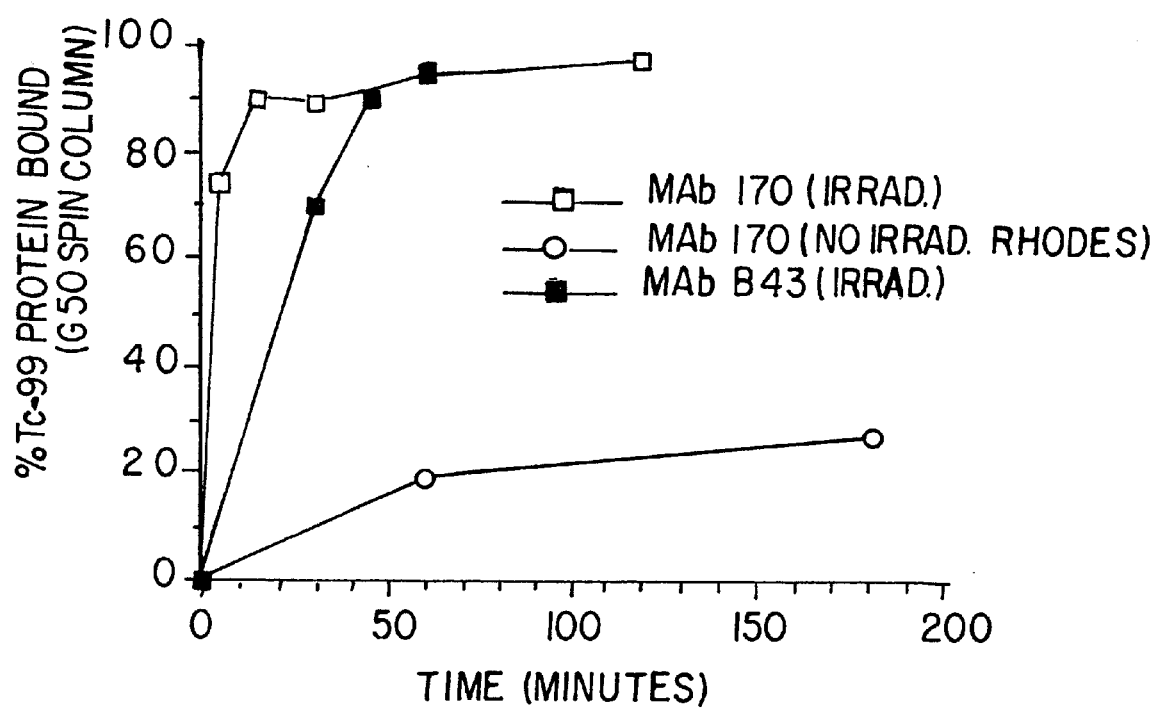
FIG. 2 shows the effect of UV irradiation on radiolabeling of Mab 170 (white squares) and Mab B43 (black squares). These are compared with the radiolabeling of MAb 170, non-irradiated, when labeled by the Rhodes method (white circles). The ordinate is the % Tc-99m which is protein bound, as measured by a G50 spin column, and the abscissa is time or irradiation in minutes for the irradiated antibodies, or the pretinning time for the non-irradiated antibody.

MAb 170 (6 mg/ml, 200 Al) with 5 µg of $Sn^{+2}$ ion in a 2 ml nitrogen purged borosilicate glass tubular vial was irradiated under the same setup as in method (A) above for 5 to 120 minutes. Another monoclonal antibody, MAb B43 (Biomira, Inc., Edmonton), was alsotested for suitability for Tc-99m radiolabelling with UV irradiation. MAb B43 (5 mg/ml) was irradiated for different periods of time under the same setup as in method (A) above (page 4) with 5 µg of stannous ion. An equal volume of Tc-99m sodium pertechnetate was added after the irradiation. The results are shown in FIG. 2 and Table 2A.

The results indicate that high radiolabelling yields can be obtained with UV irradiation. SE-HPLC on the 60 minute irradiation sample shows 956 monomeric IgG, confirming the results of the soft gel (Sephadex (TM) G 50 Spin) column. The optimal conditions for radiolabelling of B43 appear to be different from that of MAb 170 and this is probably due to the difference in amino acid composition of the antibodies. Note that the duration can be further reduced by increasing the intensity of irradiation (e.g., by using a higher power output JV source, by moving the reaction solution closer to the source or decreasing the thickness of the glass irradiation vessel walls).

Example 7

Effect of Protein Concentration on Tc-99m Radiolabelling of MAb 170

A series of samples of MAb 170 at 1 to 10 mg/ml with 5 µl of stannous ion in 2 ml nitrogen-purged borosilicate glass tubular vials were irradiated for 30 minutes. An equal volume of Tc-99m sodium Dertechnetate was added to each vial at the completion of irradiation and the percent radiolabelling assayed by Sephadex (TM) G-50 spin column. The percent radiolabelling yields are shown in table 3.

The results show chat the radiolabelling yield is concentration dependent and increasing the amount of protein increases the amount of radiolabelling obtained.

Example 8

Effect of Irradiation on Apparent Size of Irradiated Antibody Molecule

SE-HPLC analysis (UV 280 nm trace) (FIG. 3) of radiolabelled, irradiated MAb 170 indicates that the antibody does not undergo any alteration in apparent size.

Example 9

Evaluation of Immunoreactivity of MAb 170 after Irradiation and Radiolabelinq

The MAb was irradiated and radiolabeled under the conditions illustrated in Example 2. The immunoreactivity of untreated MAb, irradiated MAb and irradiated and radiolabeled MAb were then compared using a standard anti-idiotype RIA (described under Materials and Methods, C. RIA). The results are summarized in Table 4.

MAb 170 preparations treated by irradiation and subsequent radiolabelling with Tc-99m retain greater than 90% of their immunoreactivity indicating that the two-step process (irradiation with subsequent radiolabelling) incurs minimal damage to the antibody.

Example 10

Formation of Aggregates During Photolysis

Figure 3:
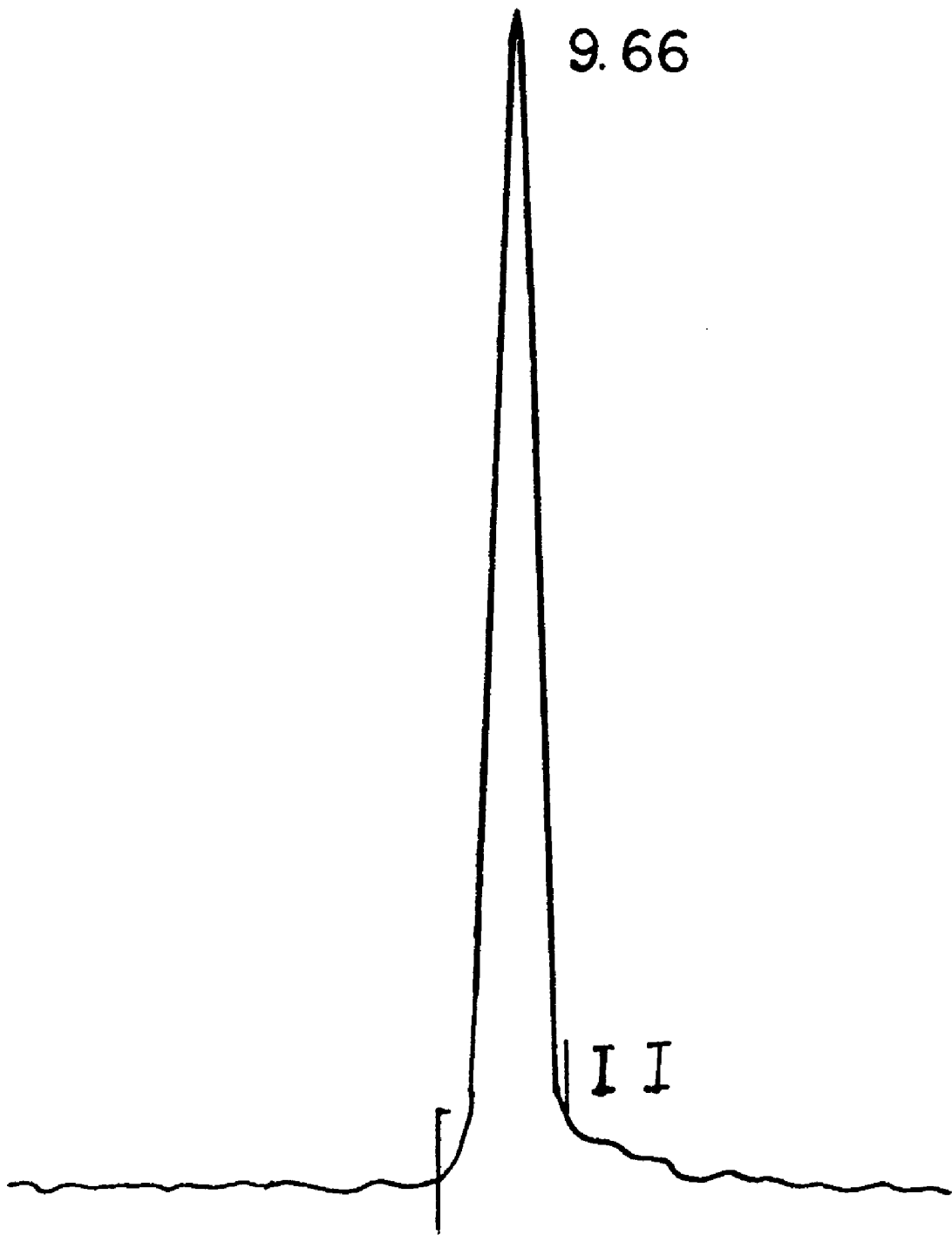
FIG. 3 shows an UV280=m chromatogram of irradiated, Tc-99m labeled MAb 170. The main peak is monomeric MAb 170 with no detectable aggregate or fragment formation. The ordinate is U absorbance at 280 nm in relative units and the abscissa is time, in minutes, after injection onto the SE-HPLC column.

MAb 170 was irradiated and radiolabeled as described in Example 3. A sample of the preparation was injected onto a SE-HPLC column and the elution profile was followed using absorbance at 280 nm. FIG. 3 shows the UV 280 nm chromatogram of this MAb and indicates that the antibody shows no aggregation (absence of a peak to the left of the main monomeric IgG peak) and minimal fragmentation (presence of a minute peak to the right of the main monomeric IgG peak).

Example 11

Effect of pH

Two experiments have been done comparing MAb 170 in either PBS (10 mM phosphate buffered saline, pH 7) or 0.1 M sodium potassium tartrate. pH 6 with irradiation at 3 cm from the water jacket for 1.5 hour and 1 hour respectively. The percent labelling efficiency for the MAb in PBS is 92.2% and for the MAb in tartrate is 91.6%. The difference is not significant. Although we have not established an absolute preference for pH it appears that for MAb 170 at least, pH is not a factor in obtaining high labelling yield.

Example 101

Studies of the Effect of UV Wavelength on Yield

Different UV light sources have been used for the photoactivation reaction. A simple Hanovia U lamp placed inside a quartz water jacket was used for the initial experiment. The principal emission from this light source was in the form of 254 nm wavelength. The Rayonet photochemical reactor was chosen for subsequent development studies, as it offers certain advantages over the Hanovia system. The Rayonet photoreactor can be fitted with 8 UV lamps inside the reactor chamber. The user can choose to turn on either 2, 4, 6 or 8 lamps, thus controlling the average intensity during the photoactivation. There is also a choice of 3 types of UV lamps covering different portion of the UV spectrum. This, coupled with the use of different types of UV filters, offers a means for studying the effect of UV wavelengths on the efficiency of the photoactivation reaction.

The photoactivation reaction is carried out in the Rayonet photochemical reactor using a quartz test-tube as the irradiation vessel. The UV light from the reactor has to pass through a 2"×2" narrow band pass-filter (254–365 nm) before it reaches the quartz tube. 0.5 mL of MAb-170 (5mg/mL in 50 mM PBS) is placed inside the quartz test-tube with 30 μg $Sn^{+2}$/mg MAb added. The solution is irradiated using different wavelength filters and then radiolabelled with Tc-99m sodium pertechnetate. The relative radiolabelling yield at each wavelength is normalized with the relative irradiation intensities at the different wavelengths.

Six experiments are described in Table 101. For each experiment, it states the filter's transmission wavelength, the nominal lamp wavelength, the lamp output, the relative lamp intensity at the transmission wavelength, and the exposure time. It should be noted that the exposure time has been chosen to compensate for differences in intensity at the transmission wavelength.

Figure 4:
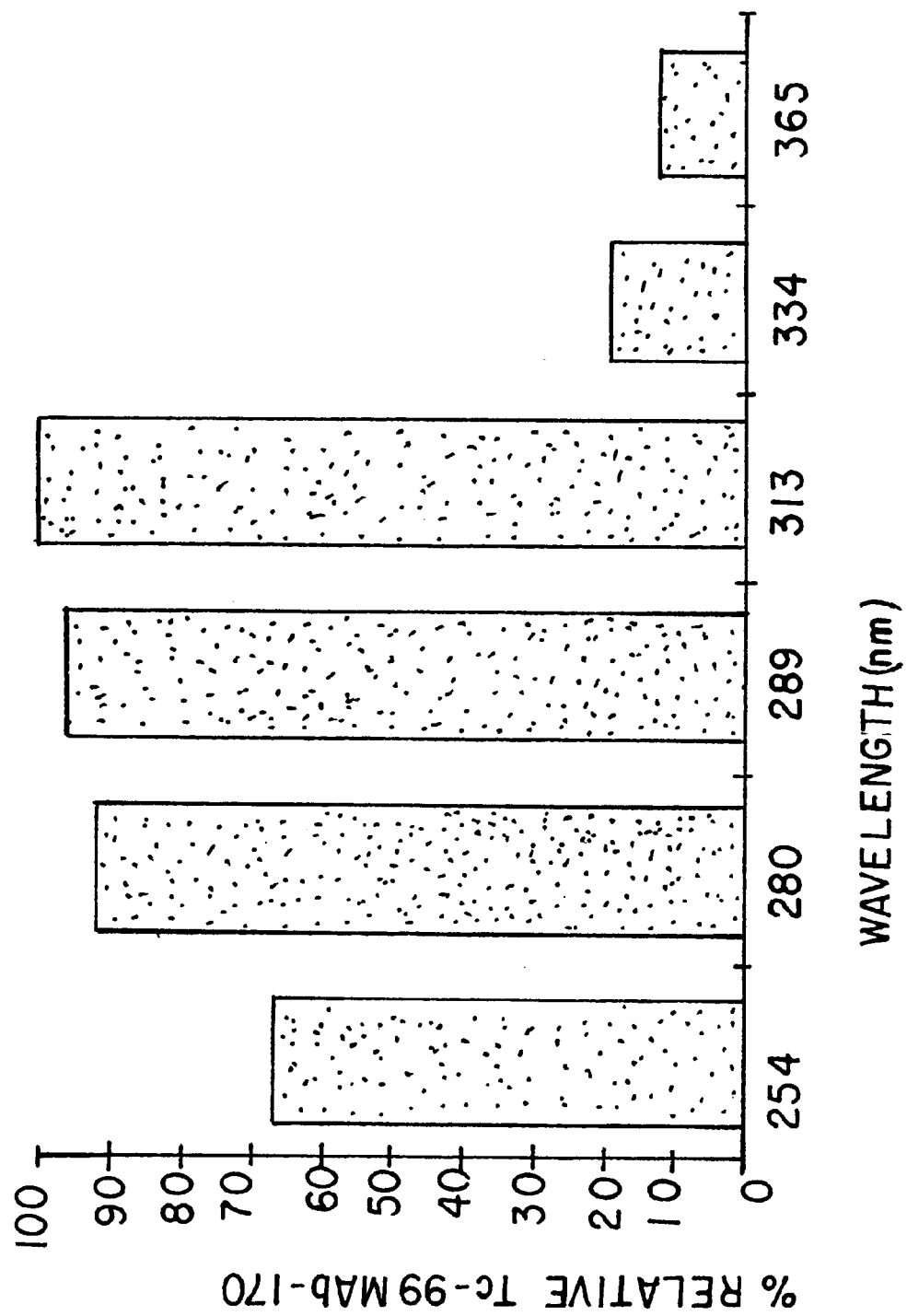
FIG. 4 shows the effect of photoactivation wavelength on radiolabeling yield.

FIG. 4 is a bar chart depicting the yield of radiolabeled antibody against the wavelength transmitted. Yield rises steadily from 254 to 313, and then dropped off sharply with an increase in wavelength to 334. Therefore, the most desirable wavelengths are in the range of 250–320 nm.

Example 102

Sulfhydryl Generation During Photoactivation

The amount of free sulphydryl generated during photoactivation is measured by reaction with Ellman's reagent. MAb-170 is photoactivated in a quartz test-tube using the Hanovia UV system. At different times post irradiation, a small aliquot is removed and allowed to react with Ellman's reagent. The UV absorbance at 412 nm is measured and the molar cysteine concentration is calculated suing a extinction coefficient of 13600.

Figure 5:
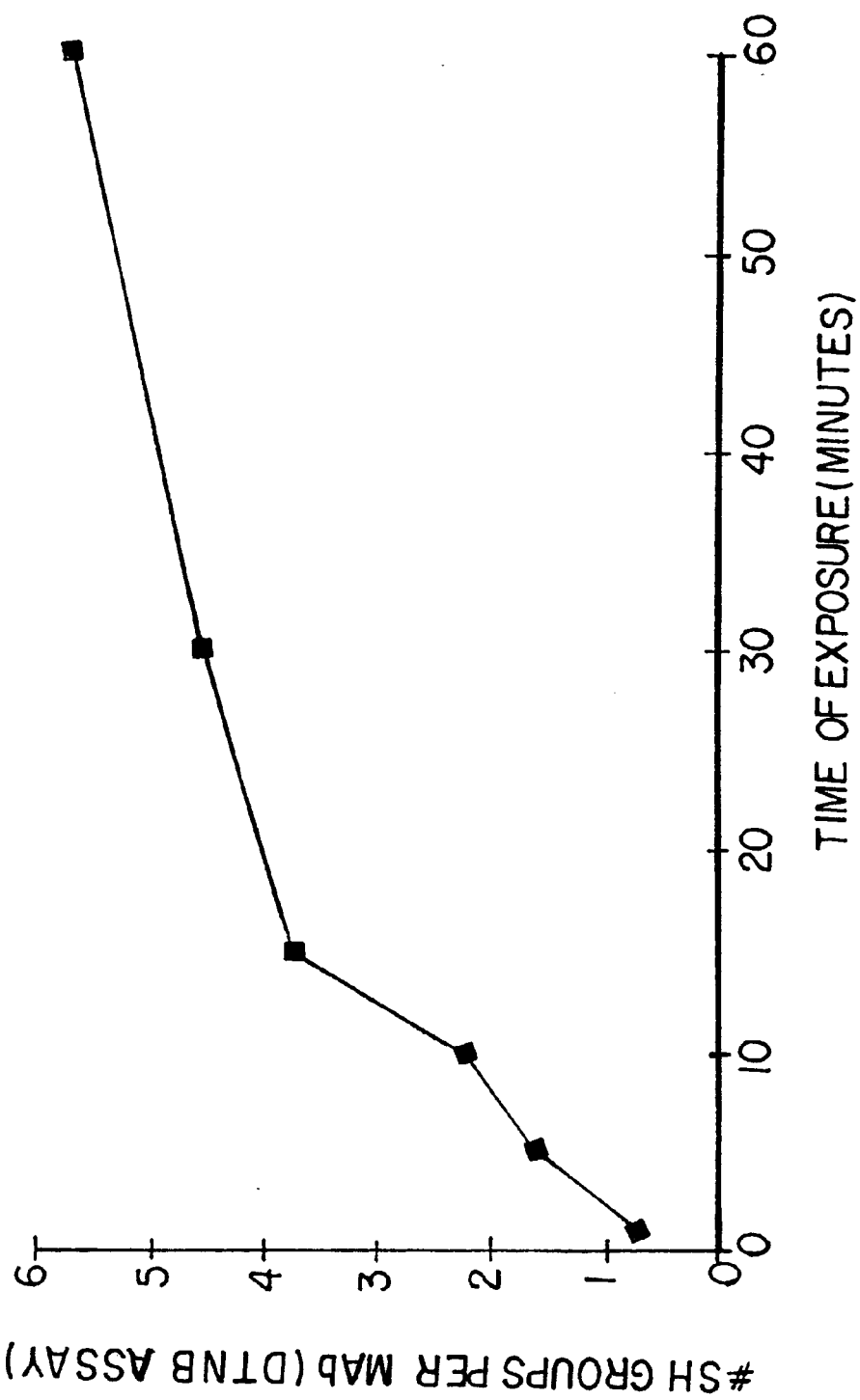
FIG. 5 depicts sulfhydryl generation as a function of the duration of the photoactivation step.

The results are shown in FIG. 5. The number of SH groups per antibody molecule increases to almost 4 in about 15 minutes. Further increases are at a slower rate, e.g., to about 5.5 in the interval from (t+15) to (t+60) mins.

Example 103

Effect of Sulfhydryl Blocking on Labeling Yield

Free sulphydryl groups can be readily blocked by sulphydryl-reactive chemicals such as iodoacetamide and N-ethylmaleimide. A drop in radiolabelling yield after blocking the sulphydryl is an indication that the sulphydryl plays a role in the radiolabelling reaction.

MAb-170 (5 mg/mL in 0.1 M tartrate buffer) is placed in a 2 mL borosilicate glass vial. The vial was capped, crimped and purged with nitrogen for 1 minute and irradiated at 300 nm for 10 to 15 minutes. The radiolabelling was then performed at a 1:1 ratio with Tc-99m sodium pertechnetate using 5–10 μg Sn/mg MAb. For the blocking, either 20 mM of iodoacetamide or 20 mM of N-ethylmaleimide was added immediately after irradiation and allowed to incubate for 15 to 30 minutes before radiolabelling. The radiolabelling yield was determined with SE-HPLC.

Figure 6:
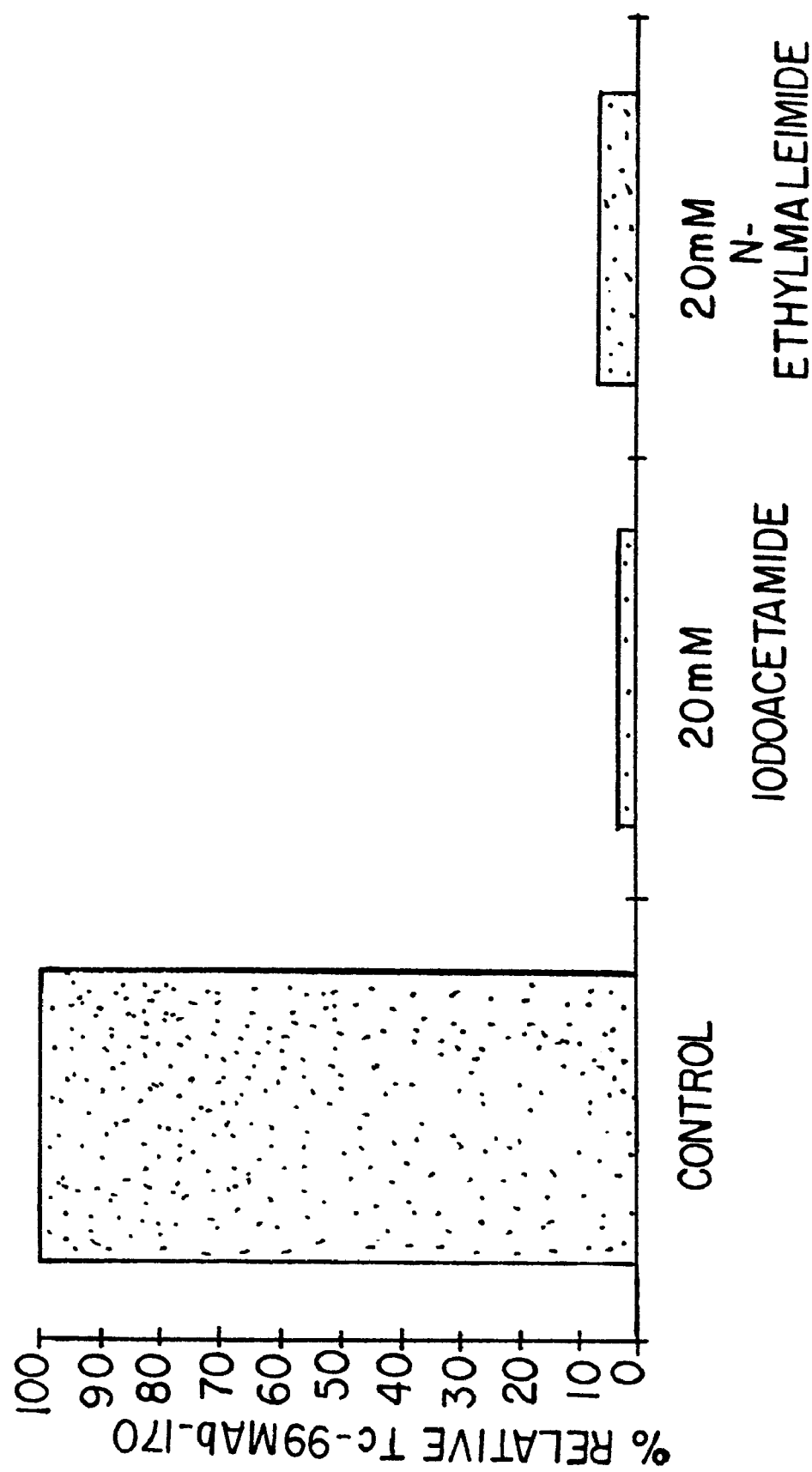
FIG. 6 shows the effect of sulfhydryl blocking agents on radiolabeling yield.

The results of sulfhydyl blocking with iodacetamide (IA) or N-ethylmaleimide (NEN) are shown in Table 102 and FIG. 6.

The data clearly indicates the importance of the generation of free sulfhydryls to radiolabelling.

Example 104

Effect of Sulfhydryl Exchange on Labeling Yield

Another indication of the involvement of the sulphydryl group in the radiolabelling reaction can be demonstrated by the interaction ith cysteine. Sulphdryl exchange reaction may interfere with stability of the Tc—SH complex.

Tc-99M MAb-170 is prepared by either using stannous-reduction or photoactivation (30 minutes at 300nm). A 6.6 mM stock solution of cysteine in dd $H_2O$ is prepared. The Tc-99m MAb-170 is mixed with the cysteine solution to give MAb:cysteine molar ratio ranging from 1:10 to 1:900. The mixture is then analyzed by SE-HPLC at different times post incubation and the % of non-protein bound radioactivity measured.

Figure 7:
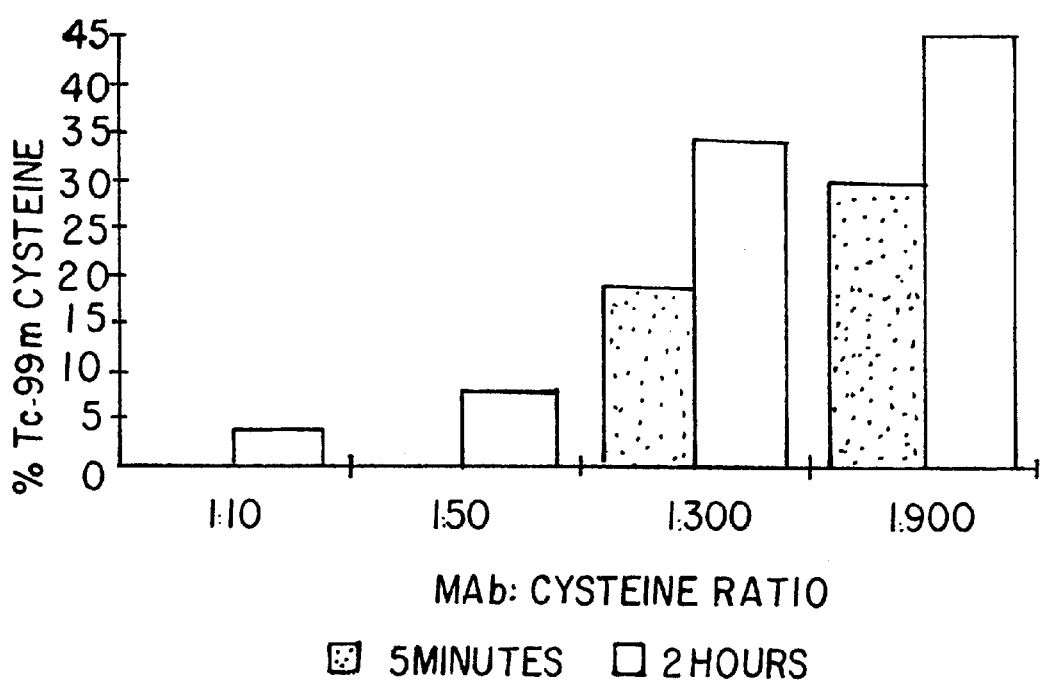
FIG. 7 considers the effect of a cysteine challenge on the photoactivation reaction, as indicated by the percentage of cysteine which is radiolabeled.
Figure 8:
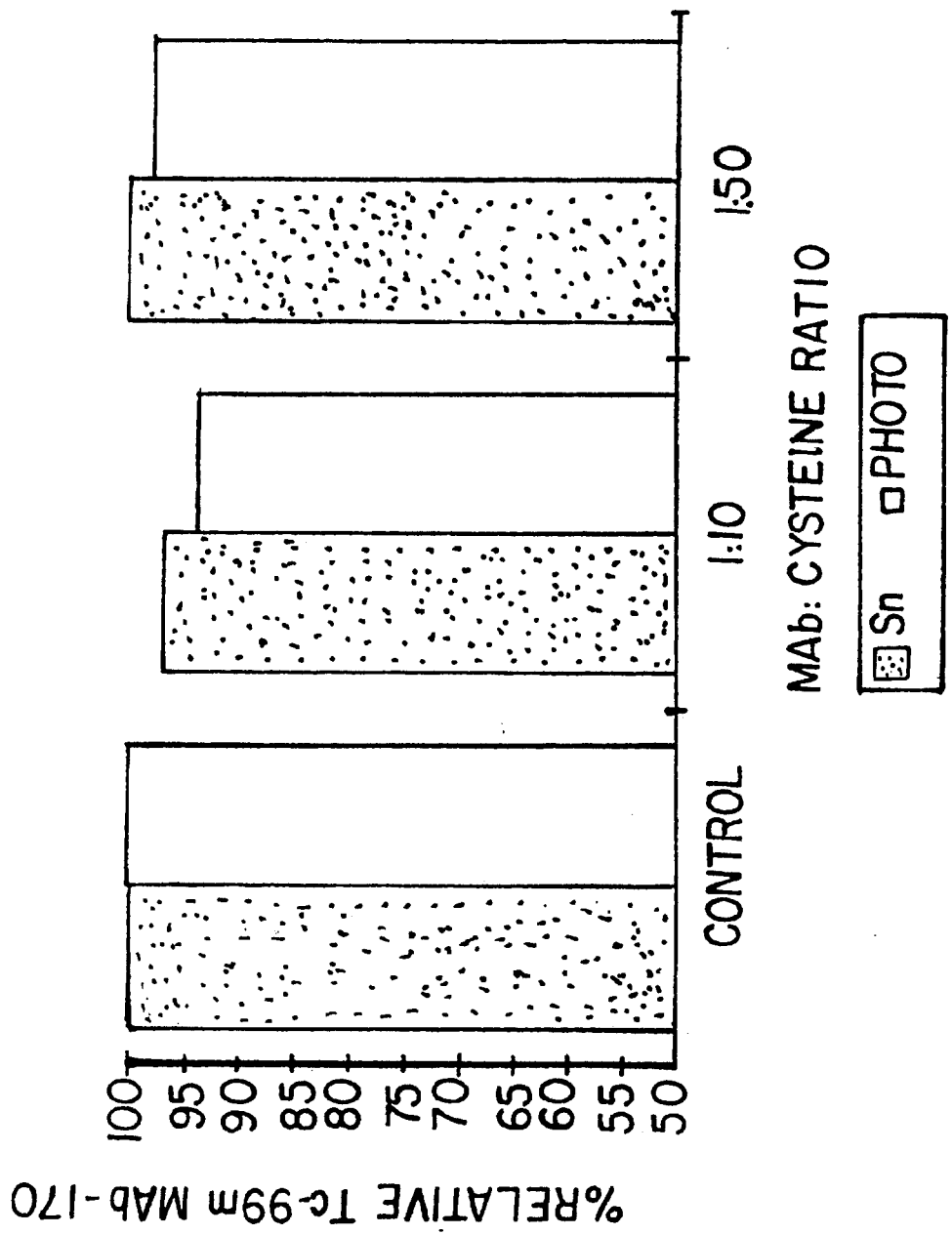
FIG. 8 compares the radiolabeling (Tc-99m) yield of stannous ion-reduced and photoactivated MAb-170 after cysteine challenge.

FIG. 7 shows the yield of radiolabeled cysteine on cysteine challenge at 5 minutes and 2 hours post-incubation for four different MAb:Cysteine ratios (1:10, 1:50, 1:300, 1:900). FIG. 8 compares the yield of radiolabeled antibody, despite cysteine challenge, for both stannous ion reduced and photoactivated antibody, at two (1:10, 1:50) different MAb:cysteine ratios. There does not appear to be significant difference between the results for the stannous ion reduced antibody and the photoactivated antibody, suggesting that the two will have similar in vitro stability with respect to cysteine transchelation.

Example 105

Effect of Stannous Sources Chosen as Pertechnetate Reducing Agent After Photoactivation In conventional methods in which stannous ion is used to reduce both the pertechnetate and the disulfide bonds of the antibody to be labeled, the choice of stannous source is of great importance. For example, in Rhodes' method, stannous phosphate cannot be used, as the complex would be too stable and the antibody therefore would not be reduced. However, we have found that a variety of stannous sources with varying levels of stannous complexing capacities can be used as the pertechnetate reducing agent after photoactivation. The amount of the stannous species should be optimized for optimal Tc-99m radiolabelling.

Several different stannous source were used as the pertechnetate reducing agent after photoactivation. A stock solution of the stannous species was prepared and assayed for its stannous content using an iodometric assay. Different levels of stannous species were added to MAb 170 and irradiated for 30 minutes at 300 nm. The Tc-99m radiolabelling yield of the photoactivated MAb is then determined by SE-HPLC.

Figure 9:
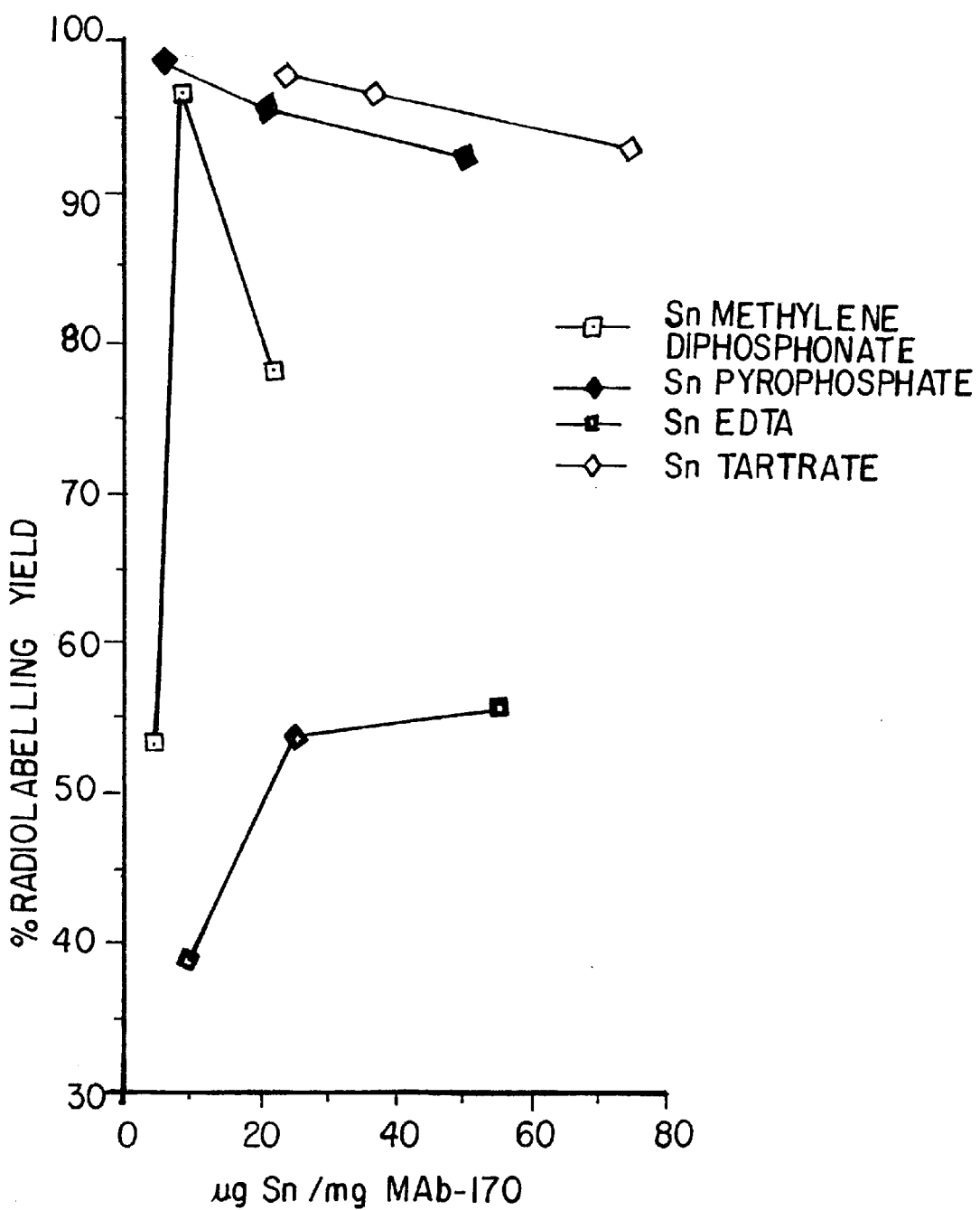
FIG. 9 plots the effect of stannous source and concentration on radiolabeling yield.

FIG. 9 shows that superior radiolabeling yields are obtained-with Sn Tartrate and Sn pyrophosphate. The yield in Sn methylene diphosphonate buffer is high for a relatively narrow range of Sn:MAb (w/w) ratios, which, however, is within the preferred range for this ratio. The yield for the reaction in Sn EDTA is consistently lower than when the reaction occurs in the two preferred buffers. While not shown on this Figure, the yield with stannous phosphate lies in between the methylene diphosphonate and the pyrophosphate data.

Example 106

Effect of MAb Buffer on Yield

MAb-170 was diafiltered into different buffer systems using the Amicon ultrafiltration cell with YM30 membrane. The buffer used included 0.1 M Tris, pH 7.5, 0.1M tartrate buffer, pH 6.0 and 0.05 M sodium acetate, pH 5.5. 500 μL of the MAb is put inside the glass with 25 μg Sn/mg MAb. The solution is irradiated for 30 minutes at 300 nm. The solution is then radiolabelled with a 1:4 (MAb:pertechnetate) ratio and analyzed by SE-HPLC.

The results are shown in Table 106. High yields were obtained with all three buffers. Given that the stannous sources mentioned in the preceding example also did not interfere with the photoactivation of the antibody, it can be surmised that any buffer which does not substantially absorb UV radiation of the preferred wavelengths can be used for the contemplated photochemical reaction. When the protein is to be labeled with technetium, and the technetium is provided in the form of pertechnate reduced with stannous ion, the buffer will also need to be compatible with the stannous ion reduction system (note that in the preceding example, the problem with EDTA was that it formed too strong a complex with the stannous ion).

Example 107

Effect of Stannous Ion Concentration on Yield

The amount of stannous ion present in the photoactivated formulation can affect the radiolabelling yield of the final product due to the competition for reduced-Tc species with the photoactivated protein. Therefore, the amount of stannous ion in the preparation should be optimized so that there is enough to carry out complete pertechnetate reduction without adversely affecting the radiolabelling yield.

Stannous phosphate solution is prepared by dissolving the stannous chloride crystals in 0.5M PBS pH 7.4. The solution is then assayed by iodometric stannous assay to determine the stannous level. The required amount of stannous phosphate solution to be added to the MAb-170 (5 mg/mL) is calculated (to give final stannous concentration of 15–30 μg Sn/mg MAb) and transferred to the MAb solution. 0.5 mL aliquots of the MAb solution is then injected into 2 mL nitrogen purged glass vials. The vials are irradiated at 300 nm for different period of time and assayed for radiolabelling yield.

Figure 10:
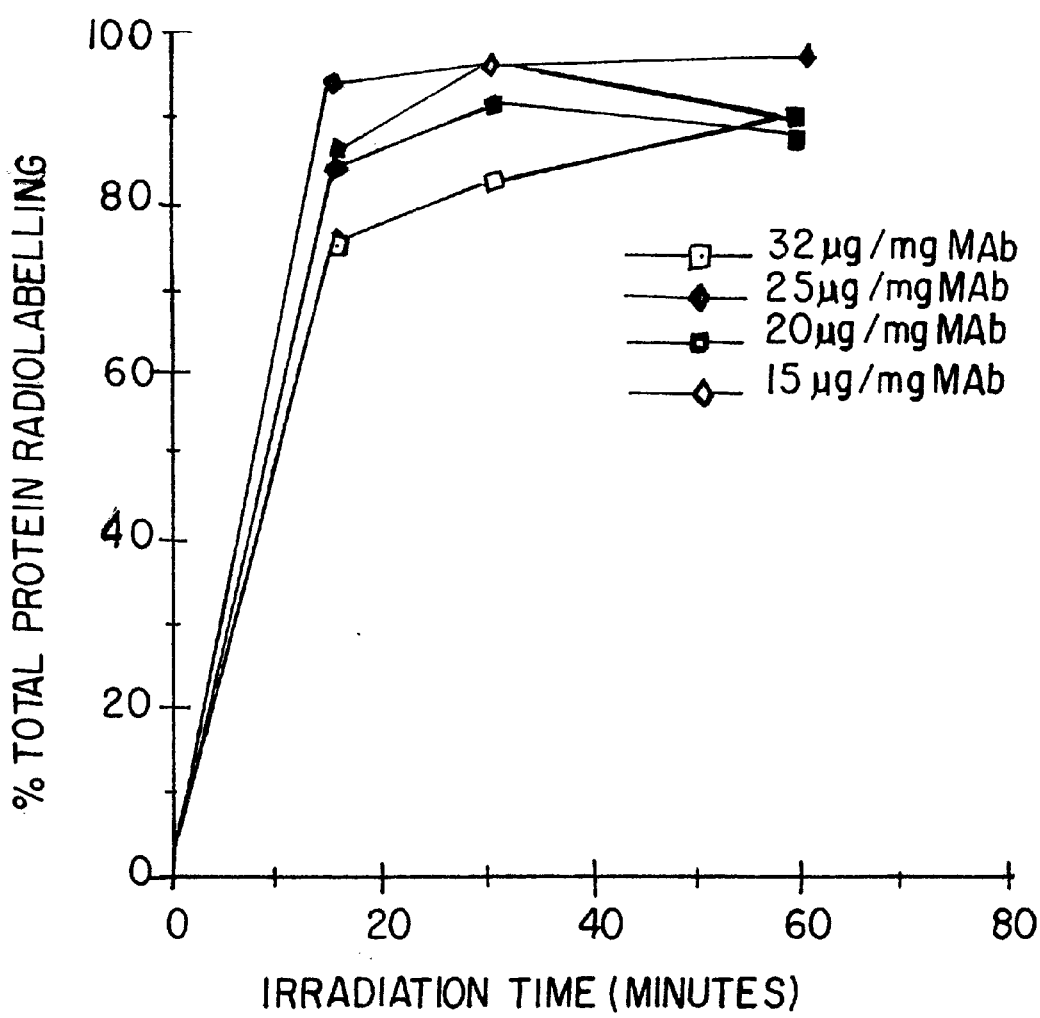
FIG. 10 depicts the effect of stannous concentration and irradiation time on radiolabeling yield.

FIG. 10 shows the radiolabeling yield, plotted against time, for four different stannous ion concentrations.

Example 108

Effect of Irradiation Volume on Yield

The kinetics of the photoactivation and subsequent radiolabelling appears to have a biphasic pattern. There is an initial rapid increase in radiolabelling yield, followed by a more gradual phase until it reaches a plateau. The change in irradiation volume during a bulk vessel irradiation is expected to alter the kinetics of the reaction due to a lowering of average irradiation intensity/unit volume.

A 50 mL borosilicate glass vial (3.8×7.5 cm) is used as the irradiation vessel. Different volumes (5, 20, 40 mL) of MAb 170 containing 25–30 μg Sn/mg MAb is added to the vial. The vial is then capped, crimped and purged with nitrogen. The vial is irradiated at 300 nm and samples are removed at different time period to assay for radiolabelling yield.

Figure 11:
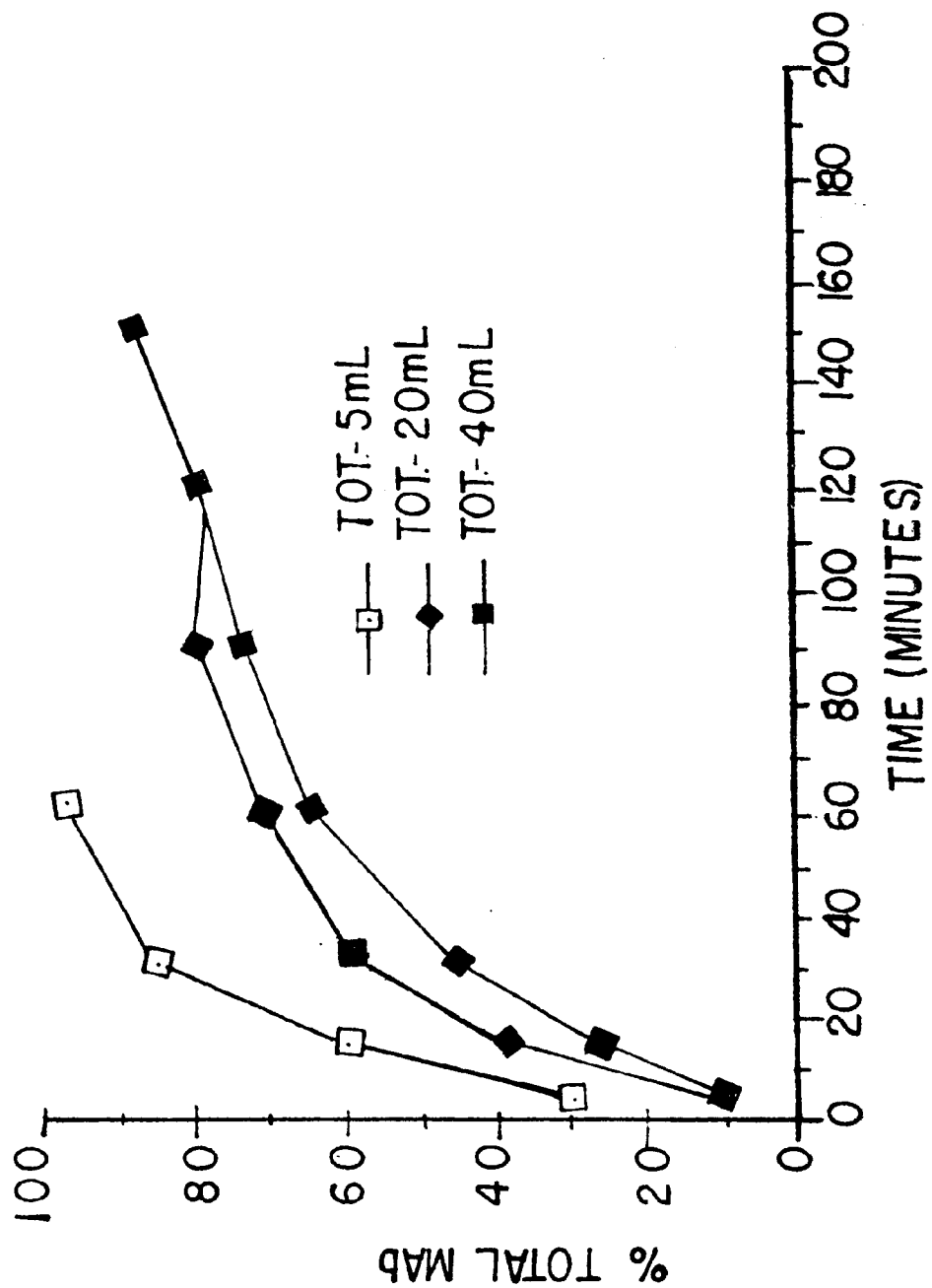
FIG. 11 is a study of the effect of irradiation volume and irradiation time on radiolabeling yield.
Figure 12A:
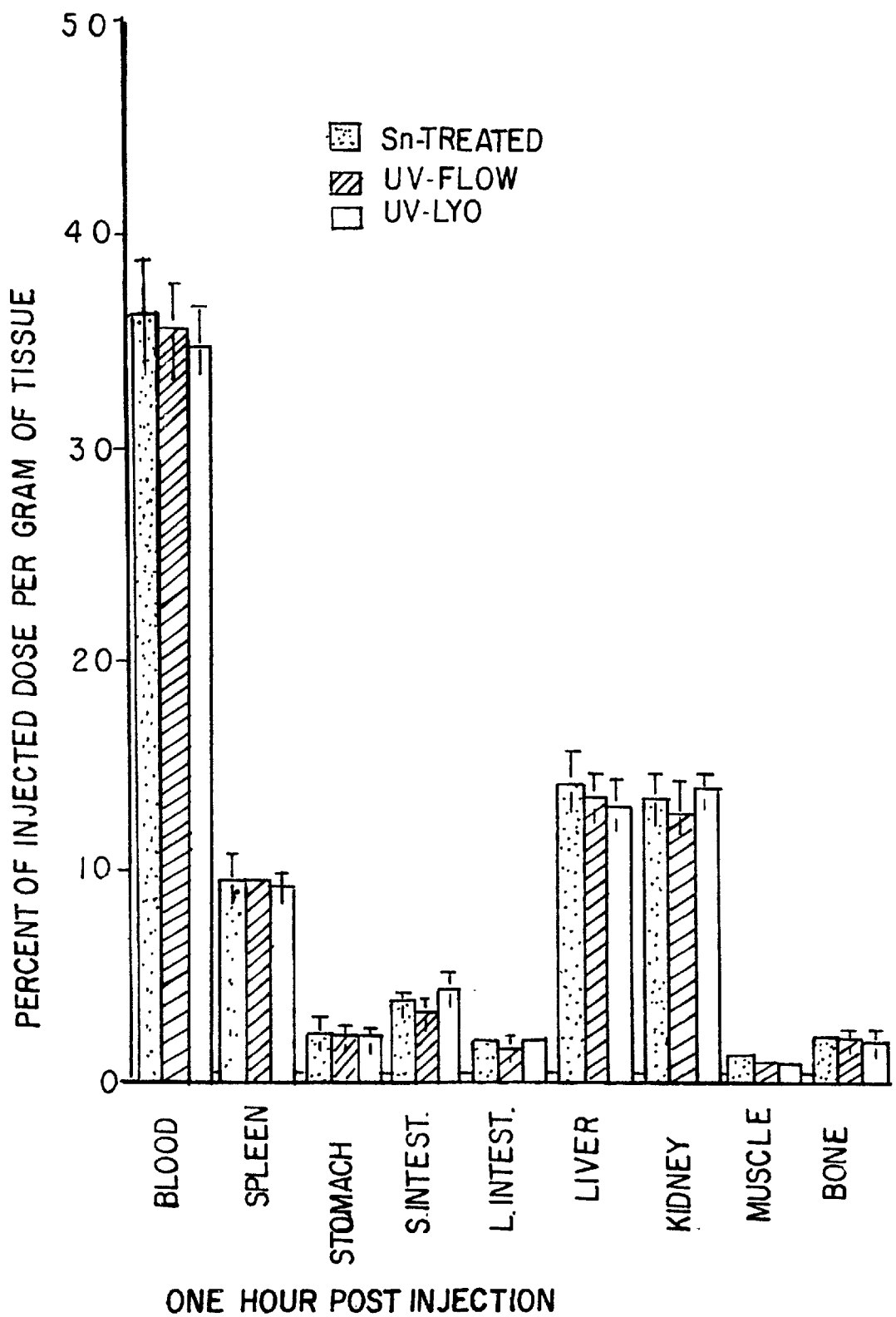

The results are shown in FIG. 11. As expected, smaller irradiation volumes result in higher yields.

Example 109

Labeling of Proteins, Other than Antibodies, by Photoactivation

The use of a photoactivation reaction for Tc-99m radiolabelling is not limited to monoclonal antibodies; other cystine containing proteins have also been radiolabelled with Tc-99m using this method. Thus, photoactivation has the potential for use with a variety of proteins and peptide structures. The conditions to obtain optimal radiolabelling yield may be different for different proteins due to the variability in the cystine and other amino acid contents and also the tertiary structure of the molecule.

In the comparative labeling experiment of Table 109, all proteins are in 50 mM PBS buffer, pH 7.4. 0.2 to 0.25 mL of protein solution containing 5 to 10 micro-g of Sn/mg protein were injected into a 2 mL glass vial. The samples were irradiated at 300 nm and subsequently radiolabelled with Tc-99m sodium pertechnetate. The protein solution in the control vial has the same amount of stannous ion but was not exposed to UV irradiation.

The results are shown in Table 109. The yield of radiolabeled transferrin and BSA is comparable to that for the three radiolabeled monoclonal antibodies.

Example 110

Small Scale Photoactivation by Individual Vial Irradiation

Due to the simplicity of the method, photoactivation can be performed in a variety of configurations, from the simple individual vial irradiation using less than 1 mg of material up to grams scale for production purposes using either a bulk-vessel or a flow-through irradiation system. The sterility of the product can be easily maintained since a close irradiation system can be used during the reaction and no complicated post-reaction purification is required. Consequently, this method can be easily adapted for use in routine research laboratory or for scale-up production in the pharmaceutical industries.

The photoactivation is performed using a Rayonet photochemical reactor with 8×300 nm UV lamps installed. Precrimped borosilicate glass sterile, empty vials (2 mL) were purchased from Hollister Stier (Canada). The vials are purged with nitrogen to maintain an inert atmosphere. A Rayonet merry-go-round unit is used as the sample holder which can accomodate up to 8 vials at a time. The unit is lowered into the cavity of the photoreactor and rotates inside the chamber to ensure uniform irradiation of all vials.

MAb-170 (5 mg/mL) is mixed with stannous phosphate (30 $\mu$g Sn$^{+2}$/mg MAb in 0.5 M phosphate buffer) and 1 mg aliquot (~0.2 mL) is injected into the sealed vials using a sterile disposable syringe. The vials are loaded onto the merry-go-round unit and lowered into the chamber of the photoreactor. The vials are allowed to irradiate for 45 minutes rotating inside the chamber cavity. At the end of the irradiation time, the vials are removed from the chamber, labelled with the contents and then store frozen at $-20°$ C.

A control set is also prepared with the same amount of MAb-170 and stannous phosphate, incubated for the same period of time but without any photoactivation. The radiolabelling yields for both sets of MAb-170 are determined by SE-HPLC using on-line radioactivity detection.

Example 111

Photoactivation by Bulk Irradiation

For reactions requiring a larger scale, single bulk irradiation vessel can be used as the reaction vessel. Efficient mixing of the solution inside the vessel is required to ensure uniform irradiation. The size of the reaction vessel is determined by the space available inside the photoreacter chamber. With our current photoreactor, a 300 mL vessel can be efficiently irradiated inside the chamber giving us a scale of up to 1.5 grams (using MAb at 5 mg/mL).

(a) Photoactivation of MAb-170 using Bulk Vessel Irradiation

A 300 mL quartz bottle with 2 side arms ports is used as the reaction vessel. MAb-170 (60 mL at 5 mg/mL, 300 mg total) are mixed with stannous phosphate (30 4g Sn$^{+2}$/mg MAb in 0.5 M phosphate buffer). The MAb solution is poured into the quartz vessel with a magnetic stir bar and lowered onto a magnetic stirrer located inside the photoreactor. The headspace of the vessel is purged with nitrogen during the irradiation, using the two side-arm ports. The solution is stirred during the irradiation and samples are withdrawn from the vessel at regular time-intervals and radiolabelled with Tc-99m sodium pertechnetate. The radiolabelling yield is determined by SE-HPLC. The results are shown in Table 111.

(b) Photoactivation of Human IgG (Gaminune N) with Bulk Vessel Irradiation

Human IgG (Gamimune N, Miles Canada) is diluted to 5 mg/mL with-50 mM PBS pH 7.4. The human IgG is subjected to the same treatment as in (a) above, with the results illustrated in Table 111A.

Example 112

Photoactivation in Recirculating Flow-Through System

Another option for the scale-up of the photoactivation reaction involves the use of a flow-through system for the irradiation of the protein. A glass or quartz coil can be prepared which will be located in the center of the photoreactor chamber. The protein solution can be stored in a vessel outside of the reaction chamber and the irradiation performed by pumping the solution through the coil, which is exposed to the UV light. Two variations of the format has been attempted. The first variation involves the recirculation of MAb solution through the coil back into the storage vessel. Efficient mixing of the solution is required for this procedure. Another variation involves a "one-pass" condition whereby the solution is pumped at a controlled flow-rate through the coil and collected in a separate collection bottle as the final product. The flow through irradiation allows for almost unlimited scale-up potential and eliminates the "volume effect" shown using a single irradiation vessel.

A PBS buffer (1.8 mL, 0.5 M, pH 7.4) was added to a stirred solution of MAb-170 (110 mL, 5 mg/mL). Then, 3.7 mL of a stannous phosphate solution (3.3 mg stannous/mL solution; 12.1 mg stannous) was added. The material was irradiated at room temperature in a borosilicate glass coil passing through a Rayonet mini-reactor with 8 (300 nm) UV lamps. The pump speed was 20 RPM. Sample were removed at different time intevals during the irradiation, reacted with pertechnetate, and assayed for Tc-99m radiolabelling yield. The results are shown in Table 112.

Example 113

Photoactivation in One-Pass Flow-Through System

Sample were removed at different time intervals during the irradiation and assayed for Tc-99m radiolabelling yield. Greater than 90% radiolabelling yields are routinely obtained.

Example 114

Preparation of Lyochilized Antibody

A lyophilized MAb kit can offer certain advantages such as better long-term product stability and ease of storage and shipment over a frozen formulation. The photoactivated MAb can be lyophilized using a suitable freeze-drying cycle and the product obtained retains is biological and radiochemical characteristics. An inert bulking agent is usually added to the formulation to improve the appearance of the cake structure.

MAb-170 (110 mL, 550 mg) is photoactivated according to the recirculating flow-through design. At the end of the process, inositol concentration of 0.5% (Final MAb concentration=2 mg/0.6 mL). 2 mg dose of the MAb solution is dispensed into 5 mL empty vial using an automatic dispenser and partially capped. The vials are then transferred to a Virtus lyophilizer and lyophilized according to the following cycle:

Pre-chill shelves for about 1.5 hours at −45° C.

Primary drying:

Shelf temp.=−20±1° C.

Ramp time=18 mins.

Dwell time=15 hours

Vacuum level=180 mT

Secondary drying:

Shelf temp.=25±1° C.

Ramp time=45 mins.

Dwell time=13 hours

Vacuum level=higher than 180 mT

After lyophilization, the vials are capped automatically inside the lyophilizer and crimped manually. The radiolabelling yield after lyophilization is measured by SE-HPLC. (Table 114)

Example 115

Effect of Photoactivation on Antibody Conformation and Activity

For biologically active or receptor specific molecules, it is important that the process utilized for radiolabelling should not alter the reactivity of the molecule. Furthermore, the radiolabelled molecule should be both biochemically and radiochemically pure. For routine radiopharmaceutical production, it is desirable that the product will retain stable for a reasonable period of time and that the radiolabel remain stable both in-vitro and in-vivo.

For Tc-99m radiolabelled protein using the indirect approach, the conjugation reaction either targets specific amino acids or is nonspecific (e.g. photoactivatable azido chelates). If the amino acids or conjugation targets happen to lie in the active sites of the molecules, the immunoreactivity of the molecule could be compromised Additional manipulation of the molecule post reaction, e.g., post-reaction purification, will not only lower the overal yield of the product but also increase the risk of further reduction in immunoreactivity.

(a) SDS-PAGE and IEF Profile of Photoactivated MAb-270 and MAb-174

The photoactivated MP-bs are routinely monitored for its bIochemical characteristics. SDS-PAGE (under reducina conditions) and isoelectric focusing are used to monitor the change in product oulaity. HPLC using a size exclusion column is used to quantify the extent of aggregation or fragmentation in the product.

MAb-170 and MAb-174 are photoactivated using the individual-vial irradiation. The photoactivated MAb is then frozen at −20° C. and an aliquot of the sample is removed for the analysis. SDS-PAGE and 7EF are performed according to established procedures.

(b) SE-HPLC (UV) Analysis of Photoactivated KAb=170 and MAb-174

MAb-170 and MAb-174 are photoactivated using the individual-vial irradiation. The photoactivated MAb is then frozen at −20° C. and an aliquot of the sample is removed for analysis. SE-HPLC is performed using a TSK SW3000XL analytical column (7.8×100 mm) and a TSK SW3000 guard column. The eluate is monitored for its UV absorbance at 280 nm using a Beckman programmable UV/Vis detector and integrated using the Beckman system gold software. The results are shown in Table 115A.

(c) SE-HPLC (Radiochemical) Profiles of Photoactivated MAb-170 and MAb-174

The radiochemical profile of the Tc-99m radiolabelled protein is routinely monitored by SE-HPLC which is capable of quantitating relative amounts of aggregates, nomomeric protein, fractionation products, unreacted reduced technetium complex, free pertechnetate and bound reduced technetium species.

MAb-170 and MAb-174 are photoactivated using individual vial irradiation. The photoactivated MAb are radiolabelled at a specific activity of ~30 mCi/mg with Tc-99m sodium pertechnetate. The SE=HPLC radiochemical profile are exhibited in Table 115B.

(d) Immunoreactivity of UV Irradiated and Radiolabelled MAb-170

The immunoreactivity of UV photoactivated MAb-170 is measured using two technicues An anti-idiotype RIA is used whereby the UV-treated MAb-170 will compete with 7–125 MAb-170 standard for bindina sites. A cell-line bioassay is also used to study the binding to MAb-170/bound antigen-expressing cell lines. The results For both assays on photcactivated Tc-99m M-Ab-170 is summarized in Table 115C.

(e) Stability Studies on Lyophilized Photoactivated MAb-70

The change in biochemical profile of a lyophilized formulation of MAb-170 labeled by photoactivation is summarized in Table 115D.

(f) Stability of Photoactivated Radiolabelled MAb Versus Serum Challenge

Tc-99m MAb-170 is prepared by individual vial irradiation and then radiolabelled with Tc-99m sodium pertechnetate. 6 µL of the radiolabelled MAb-170 is mixed with 300 µL of human serum and incubated at 37° C. At 24 and 48 hours post incubation, the mixture is analyzed by SE-HPLC and the MAb-associated peak is collected by a fraction collector. The amount of radioactivity in the MAb fraction is counted and expressed as a WO of total radioactivity. (Table 115E).

Example 116

Effect of Photoactivation on Biodistribution of Radiolabeled Antibody

MAb-170 is radiolabelled with Tc-99m using three different techniques. A stannous reduction technique is used according to a modified Rhodes method (Sn-treated). MAb-170 is also radiolabelled using the flow-through photoactivation technique from a frozen formulation (UV-Flow) and also from a lyophilized formulation prepared using the individual vial irradiation (UV-Lyo). 20 µg of the radiolabelled MAb are injected IV through the tail vein into normal Balb/C mice. Group of mice are sacrificed and the organ of interest dissected at different time period post injection. The biodistribution of the three different compounds are summarized in FIGS. 12A–12D.

All patents, patent applications, and publications cited in this specification, including Applicants' prior applications, are hereby incorporated by reference.

TABLE 1

Radiolabelling of BSA and Human Transferrin by UV Irradiation

| Protein/Concentration | % Protein Radiolabelling Irradiation Time (minutes) | | | |
|---|---|---|---|---|
| | 0 | 5 | 15 | 30 |
| (a) BSA | | | | |
| 1 mg/ml | 12.0 | 76.6 | 90.8 | 87.3 |
| 5 mg/ml | 36.1 | 80.7 | 75.1 | 92.2 |
| 10 mg/ml | 67.0 | 84.9 | 94.6 | 93.9 |
| (b) Human Transferrin | | | | |
| 1 mg/ml | 13.8 | 49.6 | 41.5 | 64.7 |
| 5 mg/ml | 40.5 | 61.2 | 64.4 | 85.3 |
| 10 mg/ml | 38.5 | 73.7 | 75.1 | 90.8 |

TABLE 2

Effect of amount of $Sn^{+2}$ ion on UV radiolabelling of protein

| Amount of $Sn^{+2}$ | % Radiolabelling |
|---|---|
| 5 μg | 96.9 |
| 10 μg | 95.5 |
| 20 μg | 92.1 |
| 40 μg | 84.8 |

TABLE 2A

Pecent Radiochemical Yield

| Time (hours) | MAb 170 Rhodes | MAb 170 Irradiated | MAb B43 Irradiated |
|---|---|---|---|
| 0 | 0 | 0 | 0 |
| 0.083 | ND | 74 | ND |
| 0.25 | ND | 90.5 | ND |
| 0.5 | ND | 88.6 | 70 |
| 0.75 | ND | ND | 90.3 |
| 1 | 18.8 | 94.2 | 94.5 |
| 2 | ND | 96.9 | ND |
| 3 | 26.8 | ND | ND |
| 6 | 25.5 | ND | ND |
| 12 | 33.5 | ND | ND |
| 24 | 52.2 | ND | ND |

ND - Not Done
For Rhodes method, time indicates time for pretinning process
For Irradiation method, time indicates amount of time exposed to UV prior to addition of Tc-99m.

TABLE 3

Effect of MAb 170 concentration on UV induced radiolabelling

| Concentration (mg/ml) | % Radiolabelling |
|---|---|
| 1 | 63.8 |
| 3 | 96.2 |
| 6 | 98.0 |
| 10 | 99.0 |

TABLE 4

Immunoreactivity of Irradiated MAb 170

| MAb | Treatment | Process Time (minutes) | Radioactive | Immunoreactivity Index1 |
|---|---|---|---|---|
| 170 (Ref.) | None | None | No | 1.00 |
| 170 | Irradiation | 30 | No | 0.97 |
| 170 | Irradiation | 30 | Yes | 0.91 |

1Value obtained from anti-idiotype RIA. RIA consists of tubes coated with rabbit anti-MAb 170 and subsequent competition between I-125 labeled MAb 170 and test or reference standard sample. Immunoreactivity Index derived from:

IC-50 Standard

IC-50 Sample

TABLE 51

MAJOR UV ABSORBING AMINO ACIDS
Molar Extinction Coefficient Values*

| Amino Acid | Wavelength (nm) | ε ($M^{-1} cm^{-1}$) |
|---|---|---|
| Tryptophan | 254 | 2760 ± 27 |
| | 266 | 4777 ± 14 |
| | 279 | 5579 ± 14 |
| Tyrosine | 254 | 341 ± 14 |
| | 266 | 960 ± 14 |
| | 275 | 1405 ± 7 |
| Phenylalanine | 254 | 140 ± 1 |
| | 258 | 195 ± 2 |
| | 266 | 92 ± 1 |
| Cysteine | 240 | ~300 |
| | 290 | ~40 |
| | 300 | ~25 |
| | 310 | <10 |

*Ref.: E. Mihalyi, J. Chem. Eng. Data 13:179–182, 1968

TABLE 52

MAJOR UV ABSORBING AMINO ACIDS
Relative Absorption Properties in Immunoglobulins*

| Wavelength (nm) | Estimated % Absorption by | | | |
|---|---|---|---|---|
| | TRP | TYR | PHE | CYS |
| 254 | 69.3 | 15.2 | 8.1 | 7.4 |
| 266 | 71.4 | 25.3 | 1.9 | 2.2 |
| 275–310 | 68.6 | 30.5 | 0.0 | 0.9 |

*Assuming TRP = 3.83%; TYR = 5.97%; PHE = 4.29%; CYS = 2.20%

TABLE 53

MAJOR UV ABSORBING AMINO ACIDS
Relative Absorption Properties*

| Wavelength (nm) | Estimated % Absorption by | | | |
|---|---|---|---|---|
| | TRP | TYR | PHE | CYS |
| 254 a | 75.9 | 9.4 | 6.5 | 8.3 |
| 266 b | 79.9 | 16.0 | 1.5 | 2.5 |
| 275–310 c | 79.0 | 19.9 | 0.0 | 1.1 |

*Assuming equimolar concentrations
a ε value at 254 nm + 258 nm used for PHE

TABLE 53-continued

MAJOR UV ABSORBING AMINO ACIDS
Relative Absorption Properties*

| Wavelength (nm) | Estimated % Absorption by | | | |
|---|---|---|---|---|
| | TRP | TYR | PHE | CYS |

ϵ value at 240 nm used for CYS
b ϵ value at 266 nm estimated as 150 for CYS
c ϵ value at 290 nm + 310 nm estimated at 75 for CYS

TABLE 101

WAVELENGTH EFFECTS FOR PHOTOACTIVATION WITH USE OF NARROW BAND-PASS (INTERFERENCE) FILTERS

| Filter # | Filter Transmission (λ ± 5 nm) | Nominal Lamp Wavelength (nm) | Estimated Output (watts) | Relative % | Exposure (Time Minutes) |
|---|---|---|---|---|---|
| 1 | 254 | 254 | 1.2 | 100.00 | 1.00 |
| 2 | 280 | 300 | 0.056 | 4.67 | 21.43 |
| 3 | 289 | 300 | 0.098 | 8.17 | 12.24 |
| 4 | 317 | 300 | 0.116 | 9.67 | 10.34 |
| 5 | 334 | 350 | 0.174 | 14.50 | 6.90 |
| 6 | 365 | 350 | 0.198 | 16.50 | 6.06 |

TABLE 102

ROLE OF SULPHYDRYL GROUPS IN PHOTOACTIVATION OF MAb-170 FOR Tc-99m RADIOLABELLING
Sulphydryl Blocking Agents

| Protein | Photoactivation | Post Treatment | % Relative Radiolabelled Protein |
|---|---|---|---|
| MAb-170 | 10 min./300 nm | — | 100.00 |
| | 10 min./300 nm | 20 mM IA a | 3.5 |
| MAb-170 | 10 min./300 nm | — | 100.00 |
| | 10 min./300 nm | 20 mM NEM b | 6.8 | a IA = Idoacetamide
b EM = N-Ethylmaleimide

TABLE 106

EFFECT OF MAb BUFFERS ON PHOTOACTIVATION

| Buffer | % Radiolabelling |
|---|---|
| 0.1 M Tris, pH 7.5 | 88.6% |
| Control* | 5.3% |
| 0.1 M Tartrate, pH 6.0 | 84.7% |
| Control* | 28.6% |
| 0.05 M Na acetate, pH 5.5 | 93.7% |

*Control = without photoactivation

TABLE 109

PHOTOACTIVATION OF PROTEINS FOR DIRECT Tc-99m RADIOLABELLING

| Protein | Concentration | Duration of reaction | % Radiolabelled Protein |
|---|---|---|---|
| MAb 174 | 1.8 | 5 minutes | 97.5% |
| Control | 1.8 | 5 minutes | 3.2% |
| MAb B80 | 5.0 | 5 minutes | 93.3% |
| Control | 5.0 | 5 minutes | 3.6% |
| Ch-MAb-174 | 1.5 | 10 minutes | 97.0% |
| Control | 1.5 | 10 minutes | 2.0% |
| MAb B43 | 6.0 | 10 minutes | 95.9% |
| Transferrin | 5.0 | 6 minutes | 87.7% |
| Control | 5.0 | 5 minutes | 4.4% |
| BSA | 5.0 | 15 minutes | 97.6% |

TABLE 109A

Cysteine Content of Selected Proteins

| Albumin | 5.09 g/100 g protein | (~28 cysteines [as disulfides or free sulfhydryls]/molecule of albumin) |
|---|---|---|
| Transferrin | 5.07 g/100 g protein | (~36 cysteines [as disulfides or free sulfhydryls]/molecule of transferrin) |
| IgG | 2.20 g/100 g protein | (~27 cysteines [as disulfides or free sulfhydryls]/molecule of IgG) |
| IgM | 1.58 g/100 g protein | (~122 cysteines [as disulfides or free sulfhydryls]/molecule of IgM) |
| IgA | 2.10 g/100 g protein | (~31 cysteines [as disulfides or free sulfhydryls]/molecule of IgA) |

TABLE 110

Radiolabelling yield for Tc-99m radiolabelled MAb=170 prepared by individual vial irradiation

| Sample ID | % Radiolabelling Yield |
|---|---|
| Photoactivated MAb-170 | >90% |
| Control MAb-170 | <10% |

TABLE 111

Radiolabelling yield for Tc-99m MAb-170 using bulk vessel photoactivation

| Irradiation Time | % Radiolabelling Yield |
|---|---|
| 15 minutes | 81.5% |
| 30 minutes | 92.8% |
| 45 minutes | 95.4% |
| 60 minutes | 95.8% |
| 75 minutes | 96.6% |

TABLE 111A

Radiolabelling yield of Tcc-99m Human IgG using bulk vessel photoactivation

| Irradiation Time | % Radiolabelling Yield |
|---|---|
| 5 mins. | 54.9% |
| 15 mins. | 77.4% |

TABLE 111A-continued

Radiolabelling yield of Tcc-99m Human IgG using bulk vessel photoactivation

| Irradiation Time | % Radiolabelling Yield |
|---|---|
| 30 mins. | 85.7% |
| 60 mins. | 90.7% |
| 120 mins. | 90.9% |

TABLE 112

Radiolabelling yield of Tc-99m MAb-170 using recirculation flow-through photoactivation

| Irradiation Time | % Radiolabelling Yield |
|---|---|
| Time 0 | 2.1% |
| 15 minutes | 93.0% |
| 30 minutes | 98.4% |
| 60 minutes | 95.8% |
| 90 minutes | 96.7% |

TABLE 114

| Sample | % Radiolabelling |
|---|---|
| Photoactivated Pre-Lyophilized | 94.7% |
| Photoactivated Lyopholized | 91.3% |

TABLE 115A

| Peak # | Retention Time | Identification | % UV 280 nm Absorbance |
|---|---|---|---|
| Sample #1 | | | |
| 1–3 | 5.8–6.8 min. | Aggregates | 2.64 ± 0.04% |
| 4 | 8.3 min. | Tc-99m MAb-170 | 96.29 ± 0.19% |
| 5–6 | 9.5–10.1 | Low M.W. Species | 1.07 ± 0.16% |
| Sample #2 | | | |
| 1–2 | 5.7–6.9 min. | Aggregates | 1.63 ± 0.54% |
| 3 | 8.3 min. | Tc-99m MAb-170 | 97.67 ± 0.96% |
| 4–5 | 9.4–10.2 min. | Low M.W. Species | 0.70 ± 0.42% |
| Sample #3 | | | |
| 1–2 | 5.9–7.5 min. | Aggregates | 4.42 ± 0.45% |
| 3 | 9.0 min. | Tc-99m MAb-174 | 95.19 ± 0.92% |
| 4 | 10 min. | Low M.W. Species | 0.39 ± 0.69% |

Table 115B

| Peak # | Retention Time | Identification | % UV 280 nm Absorbance |
|---|---|---|---|
| Sample #1 | | | |
| 1–2 | 5.8–7.0 min. | Aggregates | 3.21 ± 0.75% |
| 3 | 8.3 min. | Tc-99m MAb-170 | 92.12 ± 1.40% |
| 4–6 | 9.5–11.7 min. | Low M.W. Species | 4.00 ± 0.67% |
| 7 | 20.7 min. | Retained Tc-99m Species | 0.67 ± 0.02% |
| Sample #2 | | | |
| 1–2 | 5.9–7.1 min. | Aggregates | 3.82 ± 0.22% |
| 3 | 8.4 min. | Tc-99m Mab-170 | 90.11 ± 0.07% |
| 4–6 | 9.5–11.6 min. | Low M.W. Species | 4.55 ± 0.03% |
| 7–8 | 20.2–22.9 min. | Retained Tc-99m Species Sample #3 | 1.52 ± 0.18% |
| 1–2 | 5.9–7.5 min. | Aggregates | 6.03 ± 1.25% |
| 3 | 9.2 min. | Tc-99m MAb-174 | 87.09 ± 2.60% |
| 4–5 | 10.2–11.6 min. | Low M.W. Species | 5.01 ± 1.06% |
| 6–7 | 21.4–24.0 min. | Retained Tc-99m Species | 1.87 ± 0.58% |

TABLE 115C

| Parameter | Test | Method | Result | Comments |
|---|---|---|---|---|
| Immuno-chemical Quality | Immuno-reactivity | Anti-idiotype RIA | >0.8 Reference Ratio Value | Acceptable |
| | | Immuno-histo-chemical | >0.9 Reference Ratio Value | Acceptable |

TABLE 115D

| | | SEC (HPLC) | | | RIA IC50 % RATIO | |
|---|---|---|---|---|---|---|
| Time | Protein mg/vial | AG % | MAb % | FRG % | STD/SAM | IEF |
| DAY 0 | 0.92 | 8.6 | 88.7 | 2.5 | 1.0 | 6.6–7.1 |
| 2 - wk | 0.91 | 7.4 | 88.8 | 2.5 | 1.0 | 6.4–6.8 |
| 1 - mo | 0.97 | 8.8 | 89.2 | 1.9 | 0.93 | 6.2–6.9 |
| 3 - mo | 0.79 | 9.2 | 89.9 | 0.3 | 0.82 | 6.3–6.9 |

TABLE 115E

| Incubation Time | % MAb Associated Radioactivity |
|---|---|
| Control (No serum) | 95.6% |
| Time 0 | 92.5% |
| 24 hours | 93.1% |
| 48 hours | 75.6% |

We claim:

1. A method of preparing a conjugate of a protein having one or more disulfide bonds, and a partner chemical which is reactive with free thiol moieties, which comprises subjecting the protein to ultraviolet radiation of an intensity and duration sufficient to reduce at least some of the disulfide bonds of the protein to generate free thiol moieties, without causing substantial aggregation of the protein, and then reacting the resulting photoactivated protein with said partner chemical.

2. The method of claim 1 in which the protein is an antibody.

3. The method of claim 2 in which the antibody is one which preferentially recognizes a tumor-associated antigen.

4. The method of claim 1 in which the protein is a enzyme.

5. The method of claim 1 in which the protein is selected from the group consisting of albumin, transferrin and somatostatin.

6. The method of claim 1 in which the partner chemical is a drug or toxin.

7. The method of claim 1 in which the partner chemical is a chelating agent which is able to chelate a radioisotope and which further comprises a moiety reactive with free thiol.

8. The method of claim 1 in which the partner chemical is a radiometal ion, which optionally is reduced for reaction with the photoactivated protein.

9. The method of claim 8 in which the ion is a reduced pertechnetate or reduced perrhenate.

10. The method of claim 9 in which the pertechnate or perrhenate is reduced with stannous ion.

11. The method of claim 10 wherein the pertechnetate or perrhenate is reduced with stannous ion under conditions in which the stannous ion is unable to also reduce the disulfide bonds of the protein.

12. The method of claim 10 in which the reduction is with stannous ion and the reaction is carried out at a pH greater than 6, without substantial precipitation of stannous ion.

13. The method of claim 1 in which the percentage of the protein which is conjugated to the partner chemical is at least about 80%.

14. The method of any of claims 13 in which the protein is irradiated for not more than about one hour prior to reaction with the partner chemical.

15. The method of claim 1 wherein the irradiation is for more than 10 minutes.

16. The method of claim 1 wherein the ultraviolet irradiation is primarily with wavelengths in the range of 270–320 nm.

17. The method of claim 1 wherein the partner chemical is not itself photoactivated.

18. The method of claim 1 wherein the partner chemical is not, at the time of its reaction with the photoactivated protein, a nitrene or carbene.

19. The method of claim 1 wherein the partner chemical reacts, substantially specifically, with free thiols.

20. The method of claim 1 wherein at least 90% of the ultraviolet radiation incident on said protein is of a wavelength of 270 nm or longer.

21. A method of preparing a conjugate of a protein having one or more disulfide bonds, and a partner chemical which is reactive with free thiol moieties, which comprises subjecting the protein to ultraviolet radiation of an intensity and duration sufficient to reduce at least some of the disulfide bonds of the protein to general free thiol moieties, and then reacting the resulting photoactivated protein with said partner chemical, wherein at least 90% of the ultraviolet radiation incident on said protein is of a wavelength of 270 nm or longer.

22. The method of claim 21, wherein at least 99% of the ultraviolet radiation incident on said protein is of a wavelength of 280 nm or longer.

23. The method of claim 1, wherein at least 99% of the ultraviolet radiation incident on said protein is of a wavelength of 280 nm or longer.

24. The method of claim 1 wherein an average of at least one free thiol per molecule of protein is generated.

25. The method of claim 15 wherein the irradiation is for a period of not more than about one hour.

26. The method of claim 1 wherein the bulk of the ultraviolet radiation incident on said protein is of wavelengths greater than 300 nm.

27. The method of claim 1, wherein the amount of aggregation is less than 183.

28. The method of claim 1 wherein the amount of aggregation does not exceed 8.6%.

29. The method of claim 1 wherein the yield of monomeric conjugate is at least 90%.

30. The method of claim 1 wherein the yield of monomeric conjugate is at least 95%.

31. A method of preparing a conjugate of a protein having one or more disulfide bonds, and a partner chemical which is reactive with free thiol moieties, which comprises subjecting the protein to ultraviolet radiation of an intensity and duration sufficient to reduce at least some of the disulfide bonds of the protein to generate free thiol moieties, without causing excessive fragmentation or aggregation of the protein, and then reacting the resulting photoactivated protein with said partner chemical.

32. The method of claim 31 wherein substantial aggregation would occur if the protein were irradiated, at the same intensity and duration, with ultraviolet radiation of wavelengths less than 270 nm.

33. The method of claim 31 wherein the protein was irradiated for at least about 30 min and substantial aggregation would occur if the protein were irradiated in a quartz test tube, for 30 minutes, at the same intensity, with ultraviolet radiation from a Conrad-Hanovia low pressure quartz mercury vapor lamp, Ace Cat #12128, with a water cooled quartz jacket.

34. A method of preparing a conjugate of a protein having one or more disulfide bonds, and a partner chemical which is reactive with free thiol moieties, which comprises subjecting the protein to ultraviolet radiation of an intensity and duration sufficient to reduce at least some of the disulfide bonds of the protein to generate free thiol moieties, and then reacting the resulting photoactivated protein with said partner chemical, said ultraviolet radiation having spectral characteristics substantially identical to those provided by filtering the light emitted by a Conrad-Hanovia low pressure quartz mercury-vapor lamp (Ace Cat #12128) through borosilicate glass.

35. A method of preparing a conjugate of a protein having one or more disulfide bonds, and a partner chemical which is reactive with free thiol moieties, which comprises subjecting the protein to ultraviolet radiation of an intensity and duration sufficient to reduce at least some of the disulfide bonds of the protein to generate free thiol moieties, and then reacting the resulting photoactivated protein with said partner chemical the bulk of said ultraviolet radiation being of wavelengths greater than 300 nm.

36. A method of preparing a conjugate of a protein having one or more disulfide bonds, and a partner chemical which is reactive with free thiol moieties, which comprises subjecting the protein to ultraviolet radiation of a wavelength of 270–320 nm of an intensity and duration sufficient to reduce at least some of the disulfide bonds of the protein to generate free thiol moieties, and then reacting the resulting photoactivated protein with said partner chemical wherein the ultraviolet radiation incident on said protein is of a wavelength of 270 nm or longer.

37. A method of preparing a conjugate of a protein having one or more disulfide bonds, and a partner chemical which is reactive with free thiol moieties, which comprises subjecting the protein to ultraviolet radiation of wavelengths of 270–320 nm of an intensity and duration sufficient to reduce at least some of the disulfide bonds of the protein to generate free thiol moieties, and then reacting the resulting photoactivated protein with said partner chemical wherein the ultraviolet radiation incident on said protein is primarily of wavelengths of 270 nm or longer.

38. A method of preparing a conjugate of a protein having one or more disulfide bonds, and a partner chemical which is reactive with free thiol moieties, which comprises subjecting the protein to ultraviolet radiation, of an intensity and duration sufficient to reduce at least some of the disulfide bonds of the protein to generate free thiol moieties, where such reduction is primarily attributable to UV radiation of wavelengths of 270–320 nm, and then reacting the resulting photoactivated protein with said partner chemical.

39. The method of claim 38 in which the ultraviolet radiation incident on said protein is primarily of wavelengths of 270 nm or longer.

40. A method of preparing a conjugate of a protein having one or more disulfide bonds, and a partner chemical which is reactive with free thiol moieties, which comprises subjecting the protein to ultraviolet radiation of wavelengths of 270–320 nm of an intensity and duration sufficient to reduce at least some of the disulfide bonds of the protein to generate free thiol moieties, and then reacting the resulting photoactivated protein with said partner chemical wherein the ultraviolet radiation incident on said protein is obtained by filtering emitted ultraviolet radiation through a borosilicate glass filter.

41. A method of preparing a conjugate of a protein having one or more disulfide bonds, and a partner chemical which is reactive with free thiol moieties, which comprises (a) subjecting the protein to ultraviolet radiation comprising radiation in the wavelength range of 270–320 nm, the radiation of said range being of an incident intensity and duration sufficient to reduce at least of the disulfide bonds of the protein to generate free thiol moieties, and then (b) reacting the resulting photoactivated protein with said partner chemical, where the amount of aggregation or fragmentation caused by said ultraviolet radiation is less than what would have been caused by the combination of one Sylvania GSTS-8W bulb with an average light intensity of 10.5 $\mu W/cm^2$ at 1 m, and one Sylvania FaT5/BLB-SW bulb with an average light intensity of 17 $\mu w/cm^2$ at 1 m, if said protein had been irradiated by said combination for the same duration and with same incident intensity.

42. The method of claim 41 where the amount of aggregation or fragmentation caused by the ultraviolet radiation of (a) is substantially less than that which would have been caused by said combination.

* * * * *